(12) United States Patent
Soberon-Chavez et al.

(10) Patent No.: US 8,822,157 B2
(45) Date of Patent: Sep. 2, 2014

(54) BACTERIAL PROTEINS WITH PESTICIDAL ACTIVITY

(75) Inventors: Mario Soberon-Chavez, Morelos (MX); Alejandra Bravo-De-La-Parra, Morelos (MX)

(73) Assignee: Universidad Nacional Autonoma de Mexico, Mexico City (MX)

( * ) Notice: Subject to any disclaimer, the term of this patent is extended or adjusted under 35 U.S.C. 154(b) by 0 days.

(21) Appl. No.: 13/449,027

(22) Filed: Apr. 17, 2012

(65) Prior Publication Data

US 2012/0255065 A1 Oct. 4, 2012

Related U.S. Application Data

(62) Division of application No. 11/994,822, filed as application No. PCT/IB2006/001856 on Jul. 4, 2006, now Pat. No. 8,173,871.

(60) Provisional application No. 60/697,391, filed on Jul. 8, 2005.

(51) Int. Cl.
*C12Q 1/68* (2006.01)

(52) U.S. Cl.
USPC .................................................. 435/6.12

(58) Field of Classification Search
None
See application file for complete search history.

(56) References Cited

FOREIGN PATENT DOCUMENTS

| EP | 0 731 170 | 9/1996 |
|---|---|---|
| WO | WO 01/83561 | 11/2001 |

OTHER PUBLICATIONS

Sun et al (2001, Acta Microbiol. Sin. 41:141-147).*
Guo et al (2004, Proc. Natl. Acad. Sci. USA 101: 9205-9210).*
Hill et al (1998, Biochem. Biophys. Res. Comm. 244:573-577).*
Mesnage et al, 2001, Microbiol. 147:1343-1351.*
Accession No. AAR23791 (Dec. 3, 2003) S-layer protein [*Bacillus thuringiensis*].
Accession No. AY460125 (Dec. 3, 2003) *Bacillus thuringiensis* strain CTC S-layer protein (ctc2) gene, complete cds.
Accession No. Q6SCL0 (Oct. 31, 2006) S-layer protein.
Beveridge, et al. (1997) FEMS Microbial Rev 20: 99-149.
Crickmore, et al. (1998). Microbiology and Molecular Biology Reviews 62(3): 807-813.
Guo, et al. (2008) FEMS Microbiol. Lett. 282: 1-7.
Höfte and Whiteley (Jun. 1989) Microbiological Reviews 53(2): 242-255.
Kotiranta, et al. (Oct. 1998) Infection and Immunity 66(10): 4895-4902.
Mesnage, et al. (1998) Journal of Bacteriology 180(1): 52-58.
Mignot, et al. (2002) Molecular Microbiology 43(6): 1615-1627.
Pei and Blaser (Apr. 1990) J. Clin Invest. 85: 1036-1043.
Peña, et al. (Jan. 2006) Applied and Environmental Microbiology 72(1): 353-360.
Sára and Sleytr (Feb. 2000) Journal of Bacteriology 182(4): 859-868.
Schnepf, et al. (Sep. 1998) Microbiology and Molecular Biology Reviews 62(3): 775-806.
Sun, et al. (2001) Acta Microbiol Sin. 41: 141-147.
Xu, et al. (2004) Parasitology Research 92(1): 53-7.
Zhu, et al. (2002) 42(6): 670-674 [English Abstract].
Park et al., Journal of Invertebrate Pathology, vol. pp. 54-56 (2009).
Hill et al. (1998, Bichem, Biophys. Res. Comm, 244:573-577).
Guo et al. (2004, Proc. Natl. Acad. Sci. USA 101: 9205-9210).
International Search Report for International Application No. PCT/IB2006/001856, dated Apr. 16, 2007.
John A. Mulrennan Sr., Public Health Entomology Research and Education Center (PHEREC) Annual Report for Fiscal Year 2007/2008.
Written Opinion of the International Search Authority of International Application No. PCT/IB2006/001856 (Jan. 8, 2008).

* cited by examiner

*Primary Examiner* — Anne Kubelik
(74) *Attorney, Agent, or Firm* — Hunton & Williams LLP

(57) ABSTRACT

Provided are pesticidal, particularly insecticidal, proteins which resemble S-layer proteins, as well as variants or mutants thereof, and DNAs encoding them. Further provided are methods and means for using said DNA or protein for controlling pests, particularly plant insect pests.

2 Claims, No Drawings

SEQUENCE LISTING

```
<160> NUMBER OF SEQ ID NOS: 15

<210> SEQ ID NO 1
<211> LENGTH: 3117
<212> TYPE: DNA
<213> ORGANISM: Bacillus thuringiensis
<220> FEATURE:
<221> NAME/KEY: CDS
<222> LOCATION: (325)..(2916)

<400> SEQUENCE: 1
actttattca ttttatattt gagtattact gatatattaa taatacgatt aaaagactga     60
attatcagaa tgtgtcgaat cttcttttga gaaagttctt gataacgaat ggttttgtat    120
agtatgatga acttgtttca gaaaatggta tttaaacctt atatttacat ctaacggttt    180
atatcatttt tttatgtgaa ctacttttca ttatagtatt tttgtttatg tttttattgt    240
tttatggctt ttctaactag ctagttttca aatttaatat gatgtgaaac tagtagcata    300
ttcctgaagg aggaaattta taaa atg gca aag act aac tct tac aaa aaa       351
                           Met Ala Lys Thr Asn Ser Tyr Lys Lys
                           1               5 gta atc gca ggt aca atg aca gca gca atg gta gca ggt gtt gtt tct      399
Val Ile Ala Gly Thr Met Thr Ala Ala Met Val Ala Gly Val Val Ser
10                  15                  20                  25 cca gta gca gca gca ggt aaa tcg ttc cca gac gtt cca gct ggt cat      447
Pro Val Ala Ala Ala Gly Lys Ser Phe Pro Asp Val Pro Ala Gly His
                30                  35                  40 tgg gga tta gat tct atc aat tac tta gta gat aaa ggt gca atc gaa      495
Trp Gly Leu Asp Ser Ile Asn Tyr Leu Val Asp Lys Gly Ala Ile Glu
            45                  50                  55 ggt aag cca gat ggt aca tac gct ccg gct gaa gaa att gat cgt gct      543
Gly Lys Pro Asp Gly Thr Tyr Ala Pro Ala Glu Glu Ile Asp Arg Ala
        60                  65                  70 tct gct gcg aaa att atg gca att aca tta ggt tta aaa gtt gaa gag      591
Ser Ala Ala Lys Ile Met Ala Ile Thr Leu Gly Leu Lys Val Glu Glu
    75                  80                  85 ggt gca caa cca tct ttc aaa gat gct aaa aat cat tgg gct tct aaa      639
Gly Ala Gln Pro Ser Phe Lys Asp Ala Lys Asn His Trp Ala Ser Lys
90                  95                  100                 105 tac att gca gcg gtt gaa aaa gcg ggt gtt gtt aga ggt gat ggt aaa      687
Tyr Ile Ala Ala Val Glu Lys Ala Gly Val Val Arg Gly Asp Gly Lys
                110                 115                 120 gaa aac ttc tct cca gat aaa aag att gac cgt gct tct ttc gct tct      735
Glu Asn Phe Ser Pro Asp Lys Lys Ile Asp Arg Ala Ser Phe Ala Ser
            125                 130                 135 atg atc gta ggt gct tat aac tta aaa gat aaa gtt aac ggc gag tta      783
Met Ile Val Gly Ala Tyr Asn Leu Lys Asp Lys Val Asn Gly Glu Leu
```

```
                140             145             150
gtt aca aaa ttt gaa gat tta tta gac cat tgg ggt gaa gaa aaa gct      831
Val Thr Lys Phe Glu Asp Leu Leu Asp His Trp Gly Glu Glu Lys Ala
    155             160             165 aac atc cta atc cat ctt gga ctt tct gaa gga aca gga gga aac aag      879
Asn Ile Leu Ile His Leu Gly Leu Ser Glu Gly Thr Gly Gly Asn Lys
170             175             180             185 tgg gag cca aat aaa tct gta tct cgt gca gaa gca gct aaa ttt atc      927
Trp Glu Pro Asn Lys Ser Val Ser Arg Ala Glu Ala Ala Lys Phe Ile
                190             195             200 gca gta gca gat aaa aaa tat ggc aaa aaa gat aat gca caa gca tat      975
Ala Val Ala Asp Lys Lys Tyr Gly Lys Lys Asp Asn Ala Gln Ala Tyr
            205             210             215 gta act gat gtg aaa gtt tct gaa cca acg aaa tta aca tta act ggt     1023
Val Thr Asp Val Lys Val Ser Glu Pro Thr Lys Leu Thr Leu Thr Gly
        220             225             230 act ggt tta gat aag ctt gct gct gaa gat gta act ctt gag gga gac     1071
Thr Gly Leu Asp Lys Leu Ala Ala Glu Asp Val Thr Leu Glu Gly Asp
    235             240             245 aaa gct gtt gcg att gaa gca agt gct gac ggt act tct gca gtt gta     1119
Lys Ala Val Ala Ile Glu Ala Ser Ala Asp Gly Thr Ser Ala Val Val
250             255             260             265 aca ctt ggt ggt aaa gtt gct cca aat aaa aat ctt act gta aaa gtg     1167
Thr Leu Gly Gly Lys Val Ala Pro Asn Lys Asn Leu Thr Val Lys Val
                270             275             280 aaa aat caa tca ttc gta acg aaa ttt gta tac gaa gtg aaa aaa tta     1215
Lys Asn Gln Ser Phe Val Thr Lys Phe Val Tyr Glu Val Lys Lys Leu
            285             290             295 gca gta gaa aaa ctt aca ttt gat gat gat cgt gct ggt caa gca gtt     1263
Ala Val Glu Lys Leu Thr Phe Asp Asp Asp Arg Ala Gly Gln Ala Val
        300             305             310 gct ttc aaa tta aac gat gaa aaa ggt aac gct gat gtt gaa tac tta     1311
Ala Phe Lys Leu Asn Asp Glu Lys Gly Asn Ala Asp Val Glu Tyr Leu
    315             320             325 aac tta gca gac cat gac gtc aaa ttt gta gca aat aac tta gat ggt     1359
Asn Leu Ala Asp His Asp Val Lys Phe Val Ala Asn Asn Leu Asp Gly
330             335             340             345 tca tca gca aac atc ttt gaa ggt gga gta gct act tct act aca ggc     1407
Ser Ser Ala Asn Ile Phe Glu Gly Gly Val Ala Thr Ser Thr Thr Gly
                350             355             360 aaa cta gct gtt ggc att aaa cca gct gac tac aaa gta gaa gta caa     1455
Lys Leu Ala Val Gly Ile Lys Pro Ala Asp Tyr Lys Val Glu Val Gln
            365             370             375 gtt aca aaa cgc ggt ggt tta aca gtt tct aac act ggt att att aca     1503
Val Thr Lys Arg Gly Gly Leu Thr Val Ser Asn Thr Gly Ile Ile Thr
        380             385             390 gtg aaa aac ctt gat aca cca gct tct gca atc aaa aat gct gta ttt     1551
Val Lys Asn Leu Asp Thr Pro Ala Ser Ala Ile Lys Asn Ala Val Phe
    395             400             405 gca tta gat gct gat aat gat ggt gtt gta aac tac ggt agc aaa ctt     1599
Ala Leu Asp Ala Asp Asn Asp Gly Val Val Asn Tyr Gly Ser Lys Leu
410             415             420             425 tct ggt aaa gac ttt gct tta aat agc caa aac tta gtt gtt ggt gaa     1647
Ser Gly Lys Asp Phe Ala Leu Asn Ser Gln Asn Leu Val Val Gly Glu
                430             435             440 aaa gca tct ctt aat aaa tta gtt gct aca att gct gga gaa gat aaa     1695
Lys Ala Ser Leu Asn Lys Leu Val Ala Thr Ile Ala Gly Glu Asp Lys
            445             450             455 gta gtt gat cca gga tca att agc att aag tct tca aac cac ggt att     1743
```

```
                Val Val Asp Pro Gly Ser Ile Ser Ile Lys Ser Ser Asn His Gly Ile
                        460             465             470 att tct gta gta aat aac tac att act gct gag gct gct ggt gag gca        1791
Ile Ser Val Val Asn Asn Tyr Ile Thr Ala Glu Ala Ala Gly Glu Ala
475             480             485 aca ctt act att aaa gta ggt gac gca acg aaa gat gtt aaa ttt aaa        1839
Thr Leu Thr Ile Lys Val Gly Asp Ala Thr Lys Asp Val Lys Phe Lys
490             495             500             505 gta acg act gat tct cgt aaa tta gca tca gta aaa gct aac cca gat        1887
Val Thr Thr Asp Ser Arg Lys Leu Ala Ser Val Lys Ala Asn Pro Asp
        510             515             520 aaa tta caa gtt gtt caa aat aaa aaa tta cct gtt aca ttc gta aca        1935
Lys Leu Gln Val Val Gln Asn Lys Lys Leu Pro Val Thr Phe Val Thr
                525             530             535 act gac caa tat ggc gat cca ttt ggt gct aac cca gat gca att aaa        1983
Thr Asp Gln Tyr Gly Asp Pro Phe Gly Ala Asn Pro Asp Ala Ile Lys
        540             545             550 gaa gtt ctt ccg aaa act ggt gta gtt gca gaa ggt gga tta gat gta        2031
Glu Val Leu Pro Lys Thr Gly Val Val Ala Glu Gly Gly Leu Asp Val
555             560             565 gta acg act gac tct ggt tca att ggt acg aaa aca ctt gat gtt aca        2079
Val Thr Thr Asp Ser Gly Ser Ile Gly Thr Lys Thr Leu Asp Val Thr
570             575             580             585 ggt aac gaa gta ggc gaa ggt aca gtt cac ttc caa aac ggt aac ggt        2127
Gly Asn Glu Val Gly Glu Gly Thr Val His Phe Gln Asn Gly Asn Gly
                590             595             600 gct act tta ggc tca tta tat gtg aat gta aca gaa gga aac gtg gca        2175
Ala Thr Leu Gly Ser Leu Tyr Val Asn Val Thr Glu Gly Asn Val Ala
        605             610             615 ttt aaa aac ttt gaa ctt gta tct aaa gta ggt caa tac ggt gca tca        2223
Phe Lys Asn Phe Glu Leu Val Ser Lys Val Gly Gln Tyr Gly Ala Ser
                620             625             630 cct gat aca aaa ctt gac ctt aat gtt tct gac aca gtt gca tat caa        2271
Pro Asp Thr Lys Leu Asp Leu Asn Val Ser Asp Thr Val Ala Tyr Gln
        635             640             645 tta tct aag tac act tca gat cgc gta tac tct gat cct gaa aac tta        2319
Leu Ser Lys Tyr Thr Ser Asp Arg Val Tyr Ser Asp Pro Glu Asn Leu
650             655             660             665 gaa ggt tat gca gtt gag tct aaa aac gaa aaa gta gct aca gct aaa        2367
Glu Gly Tyr Ala Val Glu Ser Lys Asn Glu Lys Val Ala Thr Ala Lys
                670             675             680 att gtt gga aat aaa gtt gtt gtt aca ggt aaa gct cca ggt aaa gtt        2415
Ile Val Gly Asn Lys Val Val Val Thr Gly Lys Ala Pro Gly Lys Val
        685             690             695 gat atc cac tta acg aaa aat ggt gca act gct ggt aaa gca act atc        2463
Asp Ile His Leu Thr Lys Asn Gly Ala Thr Ala Gly Lys Ala Thr Ile
        700             705             710 gaa atc gtc caa gag aca att gct att aaa tct gta aac ttc aaa cca        2511
Glu Ile Val Gln Glu Thr Ile Ala Ile Lys Ser Val Asn Phe Lys Pro
715             720             725 gtt caa aca gaa aac ttc gtt gag aag aaa atc aac atc ggt act gtg        2559
Val Gln Thr Glu Asn Phe Val Glu Lys Lys Ile Asn Ile Gly Thr Val
730             735             740             745 tta gag ctt gag aag agt aac ctt gat gat atc gta aaa ggt att aac        2607
Leu Glu Leu Glu Lys Ser Asn Leu Asp Asp Ile Val Lys Gly Ile Asn
                750             755             760 tta acg aaa gat aca caa cat aaa gta cgt gtt gta aaa tct ggt gac        2655
Leu Thr Lys Asp Thr Gln His Lys Val Arg Val Val Lys Ser Gly Asp
        765             770             775
```

```
gag caa ggt aaa ctt tac tta gat aga aac ggc gat gct gta ttt aac    2703
Glu Gln Gly Lys Leu Tyr Leu Asp Arg Asn Gly Asp Ala Val Phe Asn
            780                 785                 790 gct ggc gat gta aac ctt ggt tat gta aca gta tct caa aca agt gat    2751
Ala Gly Asp Val Asn Leu Gly Tyr Val Thr Val Ser Gln Thr Ser Asp
795                 800                 805 tct gca ctt cca aac ttc aag gca gac ctt tac gat act tta act act    2799
Ser Ala Leu Pro Asn Phe Lys Ala Asp Leu Tyr Asp Thr Leu Thr Thr
810                 815                 820                 825 aag tac act gac aaa ggt aca tta gta ttc aaa gta tta ggt gag aaa    2847
Lys Tyr Thr Asp Lys Gly Thr Leu Val Phe Lys Val Leu Gly Glu Lys
            830                 835                 840 gat gtt cta aca agc gaa att ggt tca caa gct gta cac gtg aac gtt    2895
Asp Val Leu Thr Ser Glu Ile Gly Ser Gln Ala Val His Val Asn Val
                845                 850                 855 ctt aac aac cca aat cta taa gtcgattata gataaagtga aaaatcagtg       2946
Leu Asn Asn Pro Asn Leu
            860 gggatgaatt cccactgatt ttttgctgt caatagcgaa agaagcctc ttgtgaaaaa    3006 tacaagaggc tcctttctat ttcttaaact taaacatatc cccactcaaa ttcgaatcac   3066 tatacacgaa caataccatg ttaatgttgt tgtctttcat gtattgatat a           3117

<210> SEQ ID NO 2
<211> LENGTH: 863
<212> TYPE: PRT
<213> ORGANISM: Bacillus thuringiensis

<400> SEQUENCE: 2

Met Ala Lys Thr Asn Ser Tyr Lys Lys Val Ile Ala Gly Thr Met Thr
1               5                   10                  15

Ala Ala Met Val Ala Gly Val Val Ser Pro Val Ala Ala Gly Lys
                20                  25                  30

Ser Phe Pro Asp Val Pro Ala Gly His Trp Gly Leu Asp Ser Ile Asn
            35                  40                  45

Tyr Leu Val Asp Lys Gly Ala Ile Glu Gly Lys Pro Asp Gly Thr Tyr
        50                  55                  60

Ala Pro Ala Glu Glu Ile Asp Arg Ala Ser Ala Ala Lys Ile Met Ala
65                  70                  75                  80

Ile Thr Leu Gly Leu Lys Val Glu Glu Gly Ala Gln Pro Ser Phe Lys
                85                  90                  95

Asp Ala Lys Asn His Trp Ala Ser Lys Tyr Ile Ala Val Glu Lys
            100                 105                 110

Ala Gly Val Val Arg Gly Asp Gly Lys Glu Asn Phe Ser Pro Asp Lys
        115                 120                 125

Lys Ile Asp Arg Ala Ser Phe Ala Ser Met Ile Val Gly Ala Tyr Asn
    130                 135                 140

Leu Lys Asp Lys Val Asn Gly Glu Leu Val Thr Lys Phe Glu Asp Leu
145                 150                 155                 160

Leu Asp His Trp Gly Glu Lys Ala Asn Ile Leu Ile His Leu Gly
                165                 170                 175

Leu Ser Glu Gly Thr Gly Gly Asn Lys Trp Glu Pro Asn Lys Ser Val
            180                 185                 190

Ser Arg Ala Glu Ala Ala Lys Phe Ile Ala Val Ala Asp Lys Lys Tyr
        195                 200                 205

Gly Lys Lys Asp Asn Ala Gln Ala Tyr Val Thr Asp Val Lys Val Ser
    210                 215                 220
```

-continued

```
Glu Pro Thr Lys Leu Thr Leu Thr Gly Thr Gly Leu Asp Lys Leu Ala
225                 230                 235                 240
Ala Glu Asp Val Thr Leu Glu Gly Asp Lys Ala Val Ala Ile Glu Ala
            245                 250                 255
Ser Ala Asp Gly Thr Ser Ala Val Val Thr Leu Gly Gly Lys Val Ala
        260                 265                 270
Pro Asn Lys Asn Leu Thr Val Lys Val Lys Asn Gln Ser Phe Val Thr
    275                 280                 285
Lys Phe Val Tyr Glu Val Lys Lys Leu Ala Val Glu Lys Leu Thr Phe
290                 295                 300
Asp Asp Asp Arg Ala Gly Gln Ala Val Ala Phe Lys Leu Asn Asp Glu
305                 310                 315                 320
Lys Gly Asn Ala Asp Val Glu Tyr Leu Asn Leu Ala Asp His Asp Val
            325                 330                 335
Lys Phe Val Ala Asn Asn Leu Asp Gly Ser Ser Ala Asn Ile Phe Glu
        340                 345                 350
Gly Gly Val Ala Thr Ser Thr Thr Gly Lys Leu Ala Val Gly Ile Lys
    355                 360                 365
Pro Ala Asp Tyr Lys Val Glu Val Gln Val Thr Lys Arg Gly Gly Leu
370                 375                 380
Thr Val Ser Asn Thr Gly Ile Ile Thr Val Lys Asn Leu Asp Thr Pro
385                 390                 395                 400
Ala Ser Ala Ile Lys Asn Ala Val Phe Ala Leu Asp Ala Asp Asn Asp
            405                 410                 415
Gly Val Val Asn Tyr Gly Ser Lys Leu Ser Gly Lys Asp Phe Ala Leu
        420                 425                 430
Asn Ser Gln Asn Leu Val Val Gly Glu Lys Ala Ser Leu Asn Lys Leu
    435                 440                 445
Val Ala Thr Ile Ala Gly Glu Asp Lys Val Val Asp Pro Gly Ser Ile
450                 455                 460
Ser Ile Lys Ser Ser Asn His Gly Ile Ile Ser Val Val Asn Asn Tyr
465                 470                 475                 480
Ile Thr Ala Glu Ala Ala Gly Glu Ala Thr Leu Thr Ile Lys Val Gly
            485                 490                 495
Asp Ala Thr Lys Asp Val Lys Phe Lys Val Thr Thr Asp Ser Arg Lys
        500                 505                 510
Leu Ala Ser Val Lys Ala Asn Pro Asp Lys Leu Gln Val Val Gln Asn
    515                 520                 525
Lys Lys Leu Pro Val Thr Phe Val Thr Thr Asp Gln Tyr Gly Asp Pro
530                 535                 540
Phe Gly Ala Asn Pro Asp Ala Ile Lys Glu Val Leu Pro Lys Thr Gly
545                 550                 555                 560
Val Val Ala Glu Gly Gly Leu Asp Val Val Thr Thr Asp Ser Gly Ser
            565                 570                 575
Ile Gly Thr Lys Thr Leu Asp Val Thr Gly Asn Glu Val Gly Glu Gly
        580                 585                 590
Thr Val His Phe Gln Asn Gly Asn Gly Ala Thr Leu Gly Ser Leu Tyr
    595                 600                 605
Val Asn Val Thr Glu Gly Asn Val Ala Phe Lys Asn Phe Glu Leu Val
610                 615                 620
Ser Lys Val Gly Gln Tyr Gly Ala Ser Pro Asp Thr Lys Leu Asp Leu
625                 630                 635                 640
```

```
Asn Val Ser Asp Thr Val Ala Tyr Gln Leu Ser Lys Tyr Thr Ser Asp
                645                 650                 655
Arg Val Tyr Ser Asp Pro Glu Asn Leu Glu Gly Tyr Ala Val Glu Ser
            660                 665                 670
Lys Asn Glu Lys Val Ala Thr Ala Lys Ile Val Gly Asn Lys Val Val
        675                 680                 685
Val Thr Gly Lys Ala Pro Gly Lys Val Asp Ile His Leu Thr Lys Asn
    690                 695                 700
Gly Ala Thr Ala Gly Lys Ala Thr Ile Glu Ile Val Gln Glu Thr Ile
705                 710                 715                 720
Ala Ile Lys Ser Val Asn Phe Lys Pro Val Gln Thr Glu Asn Phe Val
                725                 730                 735
Glu Lys Lys Ile Asn Ile Gly Thr Val Leu Glu Leu Glu Lys Ser Asn
            740                 745                 750
Leu Asp Asp Ile Val Lys Gly Ile Asn Leu Thr Lys Asp Thr Gln His
        755                 760                 765
Lys Val Arg Val Val Lys Ser Gly Asp Glu Gln Gly Lys Leu Tyr Leu
    770                 775                 780
Asp Arg Asn Gly Asp Ala Val Phe Asn Ala Gly Asp Val Asn Leu Gly
785                 790                 795                 800
Tyr Val Thr Val Ser Gln Thr Ser Asp Ser Ala Leu Pro Asn Phe Lys
                805                 810                 815
Ala Asp Leu Tyr Asp Thr Leu Thr Thr Lys Tyr Thr Asp Lys Gly Thr
            820                 825                 830
Leu Val Phe Lys Val Leu Gly Glu Lys Asp Val Leu Thr Ser Glu Ile
        835                 840                 845
Gly Ser Gln Ala Val His Val Asn Val Leu Asn Asn Pro Asn Leu
    850                 855                 860

<210> SEQ ID NO 3
<211> LENGTH: 34
<212> TYPE: DNA
<213> ORGANISM: Artificial Sequence
<220> FEATURE:
<223> OTHER INFORMATION: PCR primer

<400> SEQUENCE: 3
acgctctaga tagcaggtaa atcattccca gacg                          34

<210> SEQ ID NO 4
<211> LENGTH: 33
<212> TYPE: DNA
<213> ORGANISM: Artificial Sequence
<220> FEATURE:
<223> OTHER INFORMATION: PCR primer

<400> SEQUENCE: 4
acgctctaga tcgccgtatt ggtcagttgt tac                           33

<210> SEQ ID NO 5
<211> LENGTH: 30
<212> TYPE: DNA
<213> ORGANISM: Artificial Sequence
<220> FEATURE:
<223> OTHER INFORMATION: PCR primer

<400> SEQUENCE: 5
gctctagatg agagtgcttt ataggaaaat                               30
```

```
<210> SEQ ID NO 6
<211> LENGTH: 31
<212> TYPE: DNA
<213> ORGANISM: Artificial Sequence
<220> FEATURE:
<223> OTHER INFORMATION: PCR primer

<400> SEQUENCE: 6
gctctagatc ttcagccgga gcgtatgtac c                              31

<210> SEQ ID NO 7
<211> LENGTH: 31
<212> TYPE: DNA
<213> ORGANISM: Artificial Sequence
<220> FEATURE:
<223> OTHER INFORMATION: PCR primer

<400> SEQUENCE: 7
gctctagata ctgctgaggc tgctggtgag g                              31

<210> SEQ ID NO 8
<211> LENGTH: 30
<212> TYPE: DNA
<213> ORGANISM: Artificial Sequence
<220> FEATURE:
<223> OTHER INFORMATION: PCR primer

<400> SEQUENCE: 8
gctctagatc ctcgacctgc ttcactatca                                30

<210> SEQ ID NO 9
<211> LENGTH: 29
<212> TYPE: DNA
<213> ORGANISM: Artificial Sequence
<220> FEATURE:
<223> OTHER INFORMATION: PCR primer

<400> SEQUENCE: 9
tctttgccat ggtataaatt tcctccttc                                 29

<210> SEQ ID NO 10
<211> LENGTH: 28
<212> TYPE: DNA
<213> ORGANISM: Artificial Sequence
<220> FEATURE:
<223> OTHER INFORMATION: PCR primer

<400> SEQUENCE: 10
ttataccatg gcaaagacta actcttac                                  28

<210> SEQ ID NO 11
<211> LENGTH: 32
<212> TYPE: DNA
<213> ORGANISM: Artificial Sequence
<220> FEATURE:
<223> OTHER INFORMATION: PCR primer

<400> SEQUENCE: 11
aaaactgcag aagtaccgtc agcacttgct tc                             32

<210> SEQ ID NO 12
<211> LENGTH: 31
<212> TYPE: DNA
<213> ORGANISM: Artificial Sequence
<220> FEATURE:
<223> OTHER INFORMATION: PCR primer
```

```
<400> SEQUENCE: 12
aacgctgcag ttgtaacact tggtggtaaa g                                    31

<210> SEQ ID NO 13
<211> LENGTH: 30
<212> TYPE: DNA
<213> ORGANISM: Artificial Sequence
<220> FEATURE:
<223> OTHER INFORMATION: PCR primer

<400> SEQUENCE: 13
cgggatcctc ctcgacctgc gtcactatca                                      30

<210> SEQ ID NO 14
<211> LENGTH: 12
<212> TYPE: PRT
<213> ORGANISM: Bacillus thuringiensis

<400> SEQUENCE: 14

Ala Gly Lys Ser Phe Pro Asp Val Pro Ala Gly His
1               5                   10

<210> SEQ ID NO 15
<211> LENGTH: 19
<212> TYPE: PRT
<213> ORGANISM: Bacillus thuringiensis

<400> SEQUENCE: 15

Lys Leu Pro Val Thr Phe Val Thr Thr Asp Gln Tyr Gly Asp Pro Tyr
1               5                   10                  15

Gly Ala Asn
```

BACTERIAL PROTEINS WITH PESTICIDAL ACTIVITY

CROSS-REFERENCE TO RELATED APPLICATIONS

This application is a divisional of U.S. patent application Ser. No. 11/994,822 filed Jan. 4, 2008, which is the U.S. National Stage filing of International Application No. PCT/IB2006/001856, filed Jul. 4, 2006, which claims priority to U.S. Provisional Patent Application No. 60/697,391, filed Jul. 8, 2005, the disclosures of each of which are hereby incorporated by reference.

FIELD OF THE INVENTION

The present invention relates to the field of pest control, particularly insect control. Provided are recombinant DNA sequences encoding pesticidal proteins designated as ISLP proteins, and toxic fragments or variants thereof, which are useful to protect organisms from pest damage, such as protecting plants from insect damage. Further provided are plants comprising a nucleic acid molecule encoding an ISLP protein of the invention, as well as methods and means for using these nucleic acid sequences for reducing pest damage, such as insect damage, to plants.

BACKGROUND

The use of bacterial biopesticides such as *Bacillus thuringiensis* (Bt) is a viable alternative for insect control in agriculture and other areas (i.e. disease vectors) that will intensify the crop production in an economically sustainable and environmental friendly way. The Bt Cry proteins are highly specific, harmless to humans, vertebrates and plants, and are completely biodegradable so no residual toxic products accumulate in the environment (Schnepf et al., 1998). To date, over 200 cry genes sequences have been determined and classified in 44 families and different subclasses (Crickmore et al., 1998, 2005). Additionally, Bt produces a number of extracellular compounds that might contribute to virulence as phospholipases, proteases, chitinases and other toxins as β-exotoxin or VIP proteins (Schnepf et al., 1998).

Despite extensive research over the last decades, only a few bacterial insecticidal toxins are used on a wide scale against the most damaging insect pests in biological pest control applications, such as those using Bt-plants.

The S-layer is an ordered structure of proteinaceous paracrystalline array, which cover the surface of many archaea and eubacteria (Beveridge et al., 1997; Sara and Sleytr, 2000) and can constitute up to 15% of total cell protein. The function of S-layer proteins has not been accurately defined, but it has been proposed that these proteins are involved in cell integrity and shape maintenance. Also, it has been hypothesized that they may be involved in macromolecular exchange with the environment since they are the outermost cell envelope component (Beveridge et al., 1997). In some gram-negative pathogenic bacteria, they have been implicated in virulence and resistance to complement-mediated killing (Sara and SLeytr, 2000; Pei and Blaser, 1990). In *B. cereus*, the S-layer has been described to promote interactions with human leucocytes and with the host, contributing to the pathogenicity (Kotiranta et al., 1998). In *B. anthracis* it has been proposed that the S-layer and the capsule might cooperate in the interaction with the host (Mignot et al., 2002).

In *B. anthracis* two different S-Layer proteins (SAP and EA1) have been described (Mignot et al., 2002). The presence of these proteins is not required for normal encapsulation of the Bacilli (Mesnage et al., 1998). These proteins appear sequentially in a growth phase-dependent manner, with the synthesis of SAP preceding that of EA1 (Mignot et al., 2002). In *B. thuringiensis* subsp. *galleria* an S-Layer protein was described, SlpA, that is similar to the SAP of *B. anthracis*. The S-layer CTC protein was described in *B. thuringiensis* subsp. *finitimus* (GenBank accession number AAR23791), this protein is similar to EA1 from *B. anthracis* (Sun et al., 2001). CTC has a molecular size of 100 kDa and forms parasporal bodies during the sporulation phase of growth.

Xu et al. (2004) describe the presence of a 120 kDa protein in an SDS-PAGE analysis of a crystal/spore mixture of a sporulating *Bacillus thuringiensis* strain. Supernatant of this crystal/spore mixture, obtained after dissolution, centrifugation and dialysis, was found to prolong the survival of mice injected with an infectious blood sample of *Plasmodium berghei*. The N-terminal sequence (15 amino acids) of the 120 kDa protein showed 100% homology to that of the S-layer protein of *Bacillus thuringiensis* subsp. *galleria* (reported in Mesnage et al., 1998). The nucleotide sequence of the gene encoding this protein is not provided but is said to encode 821 amino acid residues with a deduced molecular weight of 87.5 kDa. No isolated or purified protein, nor a recombinant host producing this protein, was tested for its efficacy against *Plasmodium* infection herein. Also, the strain from which such crystal/spore mixture was isolated has not been deposited or specifically described in this paper.

SUMMARY OF THE INVENTION

Provided in this invention are isolated pesticidal ISLP proteins characterized by:

a) being specifically pesticidal to some pests and not to others, and b) having at least 50% sequence identity with a bacterial S-layer protein, as well as such proteins which have at least 50% sequence identity to the protein of SEQ ID NO:2 or a toxic fragment thereof, and which have a molecular weight of about 50 to about 120 kDa.

Also provided herein are isolated pesticidal ISLP proteins which are characterized by:

a) being specifically insecticidal to some insects and not to others, b) having at least 70% sequence identity to a bacterial S-layer protein, c) a molecular weight of about 50 to about 120 kDa, as well as such proteins which have at least 75% sequence identity to the protein of SEQ ID NO:2 or a toxic fragment thereof, and which have a molecular weight of about 50 to about 120 kDa.

Further provided in accordance with this invention is an ISLP pesticidal protein as defined above, comprising the amino acid sequence of SEQ ID NO: 2 from an amino acid position between amino acid position 1 and amino acid position 31 to amino acid position 863, or comprising the amino acid sequence of SEQ ID NO: 2 from an amino acid position between amino acid position 1 and amino acid position 531 to amino acid position 863, such as a protein comprising the amino acid sequence of SEQ ID NO: 2.

Also included herein are isolated DNA sequences encoding any of the above ISLP proteins, and chimeric genes comprising: a) a coding sequence comprising such DNA, and b) a promoter which allows expression in plant cells. In one embodiment, such chimeric gene comprises a coding sequence which is a synthetic DNA sequence that has been optimized for expression in a host plant, particularly corn, cotton, soybean, rice, oilseed rape, cauliflower, and cabbage.

Also plant transformation vectors comprising such above chimeric genes are provided herein.

In another embodiment of this invention, a transgenic plant, seed or plant cell is provided which comprise any of the above chimeric genes, particularly a plant, seed or cell of corn, cotton, soybean, rice, oilseed rape, cauliflower, and cabbage.

Also provided herein is a method of protecting plants against damage caused by plant pests, such as insect pests, feeding on the plant species to which said plants belong, comprising the step of expressing any of the above chimeric genes in cells of said plants; as well as a method of protecting plants against damage caused by plants pests, such as insect pests, feeding on the plant species to which said plants belong, comprising the step of transforming a plant cell with any of the above chimeric genes, regenerating said cell into a plant, and obtaining progeny and propagating material of said plant, such as seeds, comprising any of such chimeric genes.

Further provided in this invention is a method for killing pests, comprising contacting said pests with any of the above ISLP proteins, particularly when such pest is an insect pest; as well as a method to protect a field of plants from pests such as insects, comprising: applying any of the above ISLP proteins to a field of plants, either in the form of a pesticidal composition comprising such protein, or in the form of a recombinant organism expressing said protein, particularly wherein said organism is a transgenic plant expressing such protein.

Also provided herein is the use of any DNA encoding any of the above ISLP proteins or a toxic fragment thereof, or any of the above chimeric genes, or any of the above ISLP proteins, to control or kill pests, such as insect pests.

DETAILED DESCRIPTION OF EMBODIMENTS OF THE INVENTION

The present invention provides methods and means for reducing damage to plants caused by pests, particularly insect pests, such as lepidopteran of coleopteran insect pests. The present invention further provides novel nucleic acid sequences and proteins that are distinct from previously described nucleic acid sequences and proteins. These nucleic acids and proteins can be used for controlling pests such as insect pests, e.g., by integration and expression of at least one of these new nucleotide sequences in plants or plant cells, or by external treatment of plants or plant parts with compositions comprising the toxins encoded by these nucleic acid molecules.

The present invention provides novel pesticidal toxins derived from bacterial strains, and use thereof to control pests, such as insects.

In accordance with this invention, a "nucleic acid sequence" refers to a DNA or RNA molecule, in single- or double-stranded form, that encodes any of the ISLP proteins of this invention. The term "isolated nucleic acid sequence", as used herein, is not limited to a nucleic acid sequence in isolation, but also encompasses a nucleic acid sequence that is no longer in the natural environment where it was isolated from. Thus, an "isolated ISLP nucleic acid (sequence)" or an "isolated ISLP protein (sequence)", in accordance with this invention, includes the nucleic acid or protein (sequence) in another bacterial host, compared to the original bacterial organism, or in a plant nuclear genome.

In accordance with the present invention, the terms "protein" or "polypeptide" are used interchangeably to refer to a molecule consisting of a chain of amino acids, without reference to any specific mode of action, size, three-dimensional structure or origin. Hence, a fragment or portion of an ISLP protein of the invention is still referred to herein as a "protein". The phrase "isolated protein", as used herein, is not limited to a protein in isolation, but also encompasses a protein that is no longer in its natural environment. The natural environment of the protein refers to the environment in which the protein could be found in nature, i.e., in the strain from which the nucleotide sequence was originally isolated. For example, an isolated protein can be present in vitro, or in another bacterial host or in a plant cell, or it can be secreted from another bacterial host or from a plant cell.

In accordance with this invention, nucleic acid sequences, including DNA sequences, encoding new ISLP proteins have been isolated and characterized, and novel forms are artificially made by DNA synthesis. A specific ISLP gene described herein was designated islp1 and its encoded protein ISLP1.

In accordance with this invention, an "ISLP" or "ISLP protein" is a pesticical, particularly an insecticidal, protein of about 40 to about 250 kDa, particularly of about 50 to about 120 kDa, or between about 60 to about 100 kDa, especially a protein of about 80 or about 100 kDa, isolated or derived from bacteria, preferably bacilli, with at least 50%, at least 60%, at least 70%, at least 80%, preferably at least 85 or 90%, sequence identity or sequence similarity to a known S-layer protein, e.g., the CTC2 protein of *B. thuringiensis* CTC (GenBank accession number AAR23791), and any toxic fragments (as defined herein) or variants thereof such as pre-proteins, mature forms, or fusions to signal peptides, to selectable marker proteins, or to other pesticidal or insecticidal proteins. Variants of ISLP proteins, as used herein, include pesticidal, preferably insecticidal, proteins immunologically related to an ISLP protein, such that they are recognized by antibodies recognizing ISLPs. The ISLPs of this invention preferably originate from or are found in (or on) bacteria of the class of Bacilli within the division of Firmicutes. In another embodiment of this invention, the ISLPs of this invention originate from or are found in (or on) bacteria of the Order Bacillales. In yet another embodiment of this invention, the ISLPs of this invention originate from or are found in (or on) bacteria of the family Bacillaceae. In a further embodiment of this invention, the ISLPs originate from or are found in (or on) bacteria of the *Bacillus cereus* group, or in (or on) bacteria of the genus *Brevibacillus* or *Bacillus*, preferably *Bacillus cereus, B. sphaericus, B. anthracia, B. licheniformis* and *B. thuringiensis*. An ISLP protein in accordance with this invention can be produced in the vegetative and/or in the sporulation phase of the bacterial life cycle and in nature it is typically a secreted protein. In accordance with this invention, the toxicity of an ISLP protein is preferably specific, so that the ISLP is toxic for only some pests, preferably insects, and leaves non-target organisms, such as mammals, unaffected. In one embodiment of this invention, the ISLP protein is not toxic to mammals, or is readily degraded in mammalian digestive systems.

A "mature ISLP protein" as used herein, refers to an ISLP protein of this invention lacking its bacterial signal peptide. An ISLP protein, as used herein, can be a protein in the full-length size or can be in a truncated form as long as the pesticidal, e.g., insecticidal, or pest-controlling, e.g., insect-controlling, activity is retained, or can be a combination of several proteins or protein domains in a hybrid or fusion protein.

In one embodiment of this invention, an ISLP protein is a pesticidal protein, particularly an insecticidal protein, specifically toxic to some pests, preferably insects, which is capable of forming crystalline structures such as crystalline arrays or S-layers on the outside of a bacterial cell in nature. In an embodiment of the invention, such ISLPs can often be isolated or co-purified in a procedure for isolating bacterial, e.g., *Bacillus thuringiensis* (Bt), crystal/spore preparations, though they have no significant sequence identity, preferably less then 40%, less then 30% or less then 20% sequence identity, to known bacterial pesticidal or insecticidal toxins such as *Bacillus thuringiensis* Cry, VIP or Cyt proteins (see Crickmore et al., 1998 and 2005) or to other known pesticidal or insecticidal bacterial, such as Bt, proteins. These ISLPs are found on the outer side of the bacterial cell wall in nature, and can be released in the environment of the bacteria or spores at sporulation.

In one embodiment, an ISLP is a pesticidal, particularly insecticidal, protein comprising three S-layer homology (SLH) regions, each of such regions having at least 50%, or at least 60%, or at least 70%, particularly at least 85 or 90%, sequence identity or similarity to the S-layer homology regions in SEQ ID NO: 2. The "S-Layer homology regions" of the ISLP protein of SEQ ID NO: 2, as used herein, are the region from amino acid position 34 to 76, the region from amino acid position 95 to 136, and the region from amino acid position 162 to amino acid position 198 in SEQ ID NO: 2.

This invention also provides the use of ISLP proteins, as defined herein, for controlling or killing pests, such as insects, such as by sowing seeds or planting plants expressing an ISLP protein in a field, or by applying ISLP proteins on plants or animals to protect them from pests, such as insects. Also processes for improving yield or enhancing crop productivity are provided, which comprise the step of growing a crop comprising a DNA encoding an ISLP protein of the invention.

In accordance with this invention, a process for isolating ISLP proteins from bacilli is provided. In one embodiment, the bacilli are grown without, or without too many, subcultivation steps before isolating ISLP proteins, since prolonged subcultivation can decrease the production of ISLP proteins. Alternatively, the bacilli from which ISLPs are to be isolated, can be grown in a susceptible pest, preferably insect pest, e.g., by applying them in their digestive system or hemolymph. The ISLP proteins produced by the bacilli can then be isolated from the pest, such as an insect, e.g., from its gut or hemolymph, preferably from those pests or insects that died or showed severe growth inhibition after application of ISLP-producing bacteria. In such process, bacteria producing highly toxic ISLPs for a certain target pest, such as an insect pest, will easily be identified by their obvious effects on that target pest. Also, a preferred target pest and an in vivo target pest environment can induce higher levels of ISLP proteins. Often ISLP proteins can be isolated from the bacteria, such as from culture supernatant, particularly in sporulating cultures, after centrifugation, or like Cry proteins of *Bacillus thuringiensis* are typically enriched and isolated. As used herein, the term "bacilli" refers to rod-shaped bacteria. These include bacteria of the Bacilli, Bacillales or Bacillaceae, such as bacteria of the *Bacillus cereus* group or bacteria of the genus *Bacillus*, e.g., *Bacillus thuringiensis*.

In one embodiment of this invention, a process for isolating novel pesticidal, preferably insecticidal, ISLP proteins, particularly ISLP proteins toxic to Lepidopteran or Coleopteran insects, is provided. Such process comprises the step of screening pesticidal, preferably insecticidal, bacilli, preferably Bt, cultures for genes with high sequence similarity to ISLPs, particularly in pesticidal, e.g., insecticidal, bacilli strains, preferably Bt strains, negative for Cry or VIP genes in PCR analysis, particularly in strains showing specific toxicity to some pests, preferably insects, but not to others. Such genes with high sequence similarity will be recognized using PCR technology and ISLP-specific primers, such as primers directed to the S-layer homology regions of ISLP proteins, e.g., the S-layer homology regions of ISLP1. The corresponding gene can then be isolated and the new ISLP protein produced by recombinant expression technology.

"kDa", as used herein, refers to the size in kiloDalton of the molecular weight of a protein. "kDa", as used herein with the term about, or referring to an approximate number ("about 80 kDa"), refers to the molecular weight observed in standard SDS-PAGE/Western blotting of a protein when compared with molecular weight standards. SDS-PAGE/Western blotting is carried using standard technology. Preferably the protein or protein fragment is confirmed as an ISLP protein by means of immunological cross-reaction (e.g., Western blotting) or by its characteristics (e.g., protein characteristics typical to S-layer proteins or fragments thereof).

"S-layer protein", or "surface layer protein", as used herein, refers to a protein secreted from the cell producing it and capable of forming a crystalline array or lattice on the surface of prokaryotes, particularly bacteria. Such lattice is mostly formed by self-assembly of protein subunits on the surface of the prokaryote so that planar, crystalline layers are formed. Examples are the S-layer proteins described by Luckevich and Beveridge (1989), Sleytr and Beveridge (1999), and Mesnage et al. (2001), particularly the S-layer protein of Bt strain CTC, GenBank accession number AAR23791.

An example of an ISLP protein is the ISLP1 protein of the invention. In accordance with this invention, an "ISLP1 protein" refers to any protein comprising the smallest toxic fragment of the amino acid sequence of SEQ ID NO: 2 that retains insecticidal activity (hereinafter referred to as the "smallest ISLP1 toxic fragment"), particularly any insecticidal protein comprising the amino acid sequence of SEQ ID NO:2 from an amino acid between amino acid position 1 and amino acid position 31 to amino acid position 863, or any insecticidal protein comprising the amino acid sequence of SEQ ID NO:2 from an amino acid between amino acid position 1 and amino acid position 531 to amino acid position 863, or any insecticidal protein comprising the amino acid sequence of the insecticidal protease-digestion, particularly trypsin-digestion, fragment from the protein of SEQ ID NO: 2, particularly an about 30, about 40, about 50 or about 60 kDa protein obtained by trypsin-digestion from the mature protein of SEQ ID NO:2. Included herein are a fusion of the ISLP1 protein with a plant signal peptide, such as a chloroplast transit peptide, to make a fusion protein. This includes hybrid or chimeric proteins comprising the smallest toxic fragment of the amino acid sequence of SEQ ID NO:2. Included in the ISLP1 protein, as used herein, is an insecticidal proteolytic fragment, preferably a trypsin-digestion fragment, of the protein of SEQ ID NO. 2, or any insecticidally-effective fragment of the protein of SEQ ID NO. 2, as well as variants or equivalents thereof which have some amino acids deleted, added or replaced while still retaining all or most of the insecticidal activity of the ISLP1 protein. Also included herein is a mature ISLP protein, lacking its signal peptide, or having the signal peptide replaced by a Methionine or by a Met-Ala or Met-Asp dipeptide.

Also included in this definition are variants of the amino acid sequence in SEQ ID NO: 2, such as amino acid sequences essentially similar to SEQ ID NO: 2, having a sequence identity of at least 70%, or at least 75%, 80%, 85%, 90%, 95%, 97%, 98% or 99% at the amino acid sequence level. In the context of the present invention, "sequence identity" may be determined using pairwise alignments using the GAP program of the Wisconsin package of GCG (Madison, Wis., USA, version 10.2). The GAP program is used with the following parameters for the amino acid sequence comparisons: the 'blosum62' scoring matrix, a 'gap creation penalty' (or 'gap weight') of 8 and a 'gap extension penalty' (or 'length weight') of 2. Insecticidal proteins according to the present invention may have some amino acids added, replaced or deleted without significantly changing, or without decreasing, the insecticidal activity of the protein.

As used herein, the term "comprising" is to be interpreted as specifying the presence of the stated features, integers, steps or components as referred to, but does not preclude the presence or addition of one or more features, integers, steps or components, or groups thereof. Thus, reference herein to DNA or protein "comprising the sequence or region X" refers to a DNA or protein including or containing at least the sequence or region X, so that other nucleotide or amino acid sequences can be included at the 5' (or N-terminal) and/or 3' (or C-terminal) end. For example, a nucleotide sequence may comprise the nucleotide sequence encoding a transit peptide, and/or a 5' or 3' leader sequence.

A "toxic fragment" of an ISLP protein, as used herein, is a fragment or portion of an ISLP protein that retains some or all, preferably most, of the toxicity of the pesticidal, preferably insecticidal, mature ISLP protein. Typically, such a toxic fragment is obtained by cleavage of the signal peptide or by enzymatic digestion of the full length or mature ISLP protein, e.g., by digestion with pest, preferably insect, gut enzymes such as trypsin, chymotrypsin, or other proteases active in a target pest's digestive system, such as the target insect midgut digestive enzymes. Typically such a toxic fragment has a molecular weight of about 40 to about 80 kDa, preferably about 50 or about 60 kDa. A toxic fragment of the ISLP1 protein of this invention is a trypsin-digestion fragment of about 50 kDa. The "smallest toxic fragment" of an ISLP protein is the smallest toxic fragment of the ISLP protein. Such smallest toxic fragment can be obtained by enzymatic cleavage or by expression of islp DNA with nucleotide deletions. DNA encoding toxic ISLP fragments may also be synthesized chemically; thus, toxic fragments obtainable from transcription and translation of synthetic DNA is included in the definition of toxic fragment. Any protein comprising the smallest ISLP toxic fragment is useful in this invention, and not only the original or mature ISLP protein, since amino acid sequences not necessary for toxicity can be deleted or can be replaced by other sequences while retaining the characteristics of the ISLP protein.

Toxic fragments of ISLP proteins can also be obtained by the breakdown and solubilization of ISLP proteins at the time of autolysis of the bacteria, e.g., in a pest digestive system, such as an insect midgut, or upon sporulation in in vitro cultures. Smaller, more soluble, fragments which still are immunologically detected with anti-ISLP antibodies appear and can be identified or isolated after autolysis using routine technologies such as antibody-mediated purification.

A "target pest", as used herein, is a pest, preferably insect, which can be killed or negatively affected (e.g., its growth is inhibited) by an ISLP. This pest or insect shows toxicity above control levels, when infected or fed with bacteria producing this ISLP protein, or when fed with diet containing isolated ISLP protein.

Possible Lepidopteran target insects for ISLP proteins of the invention include, but are not limited to, corn earworm (*Helicoverpa zea*), cotton bollworm (*Helicoverpa armigera*), native budworm (*Helicoverpa punctigera*), tobacco budworm (*Heliothis virescens*), european corn borer (*Ostrinia nubilalis*), fall armyworm (*Spodoptera frugiperda*), black cutworm (*Agrotis ipsilon*), pink bollworm (*Pectinophora gossypiella*), yellow stem borer (*Scirphophaga incertulas*), leaffolder (*Cnaphalocrocis medinalis*), pink stem borer (*Sesamia inferens*), corn spotted stem borer (*Chilo partellus*), velvet caterpillar (*Anticarsia gemmatalis*), soybean looper (*Pseudoplusia includens*), pod borer (*Epinotia aporema*), and *Rachiplusia nu*.

Other possible target insects for the ISLP proteins of the invention are selected from the list consisting of: *Plathypena scabra, Spodoptera exigua, Spodoptera omithogalli, Chilo suppressalis, Hereitogramma licarisalis, Naranga aenescens, Mycalesis gotama, Marasmia patnalis, Marasmia exigua, Marasmia ruralis, Nymphula depunctalis, Scirpophaga innotata, Spodoptera litura, Chilo polychrysus, Rupela albinella, Diatraea saccharalis, Spodoptera frugiperda, Mythimna unipuncta, Chilo zacconius* and *Parnara guttata, Agelastica alni, Hypera postica, Hypera brunneipennis, Haltica tombacina, Anthonomus grandis, Tenebrio molitor, Triboleum castaneum, Dicladispa armigera, Trichispa serica, Oulema oryzae, Colaspis brunnea, Lissorhorptrus oryzophilus, Phyllotreta cruciferae, Phyllotreta striolata, Psylliodes punctulata, Entomoscelis americana, Meligethes aeneus, Ceutorynchus* sp., *Psylliodes chrysocephala, Phyllotreta undulata, Leptinotarsa decemlineata, Diabrotica undecimpunctata undecimpunctata, Diabrotica undecimpunctata howardi, Diabrotica barberi*, and *Diabrotica virgifera*.

As used herein, the term "islp DNA" or "ISLP DNA" refers to any DNA encoding an ISLP protein, such as a DNA encoding the "ISLP1 protein" as defined above, e.g., the islp1 DNA shown in SEQ ID NO: 1, particularly from nucleotide position 325 to nucleotide position 2913, preferably from nucleotide position 412 to nucleotide position 2913. This includes naturally-occurring, artificial, or synthetic DNA sequences encoding the protein of SEQ ID NO: 2, or their toxic fragments or variants as defined above. Also included herein are DNA sequences encoding insecticidal proteins, which are similar enough to a DNA encoding an ISLP protein of the invention that they can (i.e., have the ability to) hybridize to these DNA sequences under stringent hybridization conditions.

Also included in the invention are any promoters of islp genes isolated in accordance with this invention and their use, e.g., the promoter region of the islp1 DNA of SEQ ID NO: 1, which can provide powerful promoters for bacterial expression. The promoter of the islp1 DNA as used herein comprises the sequence of SEQ ID NO:1 from nucleotide position 1 to nucleotide position 324.

"Stringent hybridization conditions", as used herein, refers particularly to the following conditions: immobilizing the relevant DNA on a filter, and prehybridizing the filters for either 1 to 2 hours in 50% formamide, 5% SSPE, 2× Denhardt's reagent and 0.1% SDS at 42° C., or 1 to 2 hours in 6×SSC, 2× Denhardt's reagent and 0.1% SDS at 68° C. The denatured (Digoxigenin- or radio-) labeled probe is then added directly to the prehybridization fluid and incubation is carried out for 16 to 24 hours at the appropriate temperature mentioned above. After incubation, the filters are then washed for 30 minutes at room temperature in 2×SSC, 0.1% SDS, followed by 2 washes of 30 minutes each at 68° C. in 0.5×SSC and 0.1% SDS. An autoradiograph is established by exposing the filters for 24 to 48 hours to X-ray film (Kodak XAR-2 or equivalent) at −70° C. with an intensifying screen (20× SSC=3M NaCl and 0.3M sodium citrate; 100× Denhardt's reagent=2% (w/v) bovine serum albumin, 2% (w/v) Ficoll™ and 2% (w/v) polyvinylpyrrolidone; SDS=sodium dodecyl sulfate; 20×SSPE=3.6M NaCl, 0.2M Sodium phosphate and 0.02M EDTA pH7.7). One of ordinary skill in the art will readily be able to modify the particular conditions and parameters specified above while retaining the desired stringent hybridization conditions.

There are many approaches known in the art for the isolation of variants of the DNA sequences of the invention. For example, variants can be detected and isolated from bacterial strains, e.g., bacilli, particularly *Bacillus* spp., by hybridization as described supra, and/or by PCR technology, as known in the art. Specific or degenerate primers can be made to regions of the islp DNA sequences, and used to amplify variants from known or novel bacterial strains.

Variants of the islp DNA of the invention include DNA sequences encoding the ISLP protein variants described above, or a DNA sequence, encoding an insecticidal protein, with at least 60%, at least 65%, at least 70%, 80% or 90%, sequence identity to an islp DNA of the invention, e.g. SEQ ID NO: 1, preferably from nucleotide position 412 to nucleotide position 2913. The sequence identities referred to are calculated using the GAP program of the Wisconsin package of GCG (Madison, Wis., USA) Version 10.2. The GAP program is used with the following parameters for nucleic acids: the "nwsgapdna" scoring matrix, a "gap creation penalty" (or "gap weight") of 50 and a "gap extension penalty'" (or "length weight") of 3. Stringent hybridization conditions are as defined above.

"Insecticidal activity" of an ISLP protein, as used herein, means the capacity of such protein to kill insects when such protein is fed to insects, preferably by expression in a recombinant host such as a plant. It is understood that a protein has insecticidal activity if it has the capacity to kill the insect during at least one of its developmental stages, preferably the larval stage.

"Insect-controlling amounts" of a protein, as used herein, refers to an amount of protein which is sufficient to limit damage on a plant, caused by insects at any stage of development (e.g., insect larvae) feeding on such plant, to commercially acceptable levels. Limiting insect damage to a plant may be the result of, for example, killing the insects or inhibiting insect development, fertility or growth in such a manner that the insect inflicts less damage to a plant and plant yield is not significantly adversely affected. As used herein, to "control" insects means to obtain at least significant growth inhibition, developmental retardation or inhibition of fertility (above control values) of such insects when treated with the ISLP protein of the invention.

In accordance with this invention, insects susceptible to the new ISLP proteins of the invention are contacted with this protein in insect-controlling amounts, preferably insecticidal amounts. Preferred target insects for the proteins of this invention are economically damaging insect pests of corn, cotton, rice, soybean, vegetable plants, *Brassica* species plants, *Brassica napus*, cauliflower, carrot, pea, wheat, barley, rye, tomato, potato, sugarbeet, cut flowers, roses, fruit plants (apple, pear, peach, strawberry, etc.), trees (such as poplar and willow), and lettuce, particularly in Europe, Northern and Southern American countries, Asia and Australia. The term "plant", as used herein, encompasses whole plants as well as parts of plants, such as leaves, stems, seeds, flowers or roots.

"Pesticidal activity" of an ISLP protein, as used herein, refers to the activity of a protein to kill, cause disease, inhibit growth or otherwise negatively affect all or part of a plant or animal pest organism, such as certain Arthropods, nematodes, mites, aphids, flies, bacteria, viruses, fungi, etc. A plant or animal pest organism, as used herein, is any living organism that can cause damage to a plant or animal, including humans, by causing infections, illness or death to parts or all of the plant or animal, or otherwise inhibiting growth, disabling or negatively affecting such plant or animal, preferably these are smaller organisms such as invertebrates. A vector organism capable of passing on a pest organism to a plant or animal, is also considered a pest organism as used herein, e.g., pests such as mosquitoes or cockroaches.

The nucleic acid sequence, particularly the DNA sequence, encoding a ISLP protein of this invention can be made synthetically and can be inserted in expression vectors to produce high amounts of ISLP proteins. The ISLP proteins can be used to prepare specific monoclonal or polyclonal antibodies in a conventional manner (Hate et al., 1988; Harlow and Lane, 1988).

In one embodiment of the invention, antibodies that specifically bind to the ISLP protein are provided. In particular, monoclonal or polyclonal antibodies that bind to an ISLP protein or to fragments or variants thereof are provided. Also included are fragments of monoclonal or polyclonal antibodies, which retain the ability to bind to the ISLP protein or fragment against which they were raised (e.g., single-chain antibodies). An antibody to an ISLP protein can be prepared by using the ISLP protein as an antigen in an animal (such as rabbit or mouse), using methods known in the art. Suitable methods for preparing antibodies include those described in Harlow and Lane "Using Antibodies: A Laboratory Manual" (New York: Cold Spring Harbor Laboratory Press, 1998); and in Liddell and Cryer "A Practical Guide to Monoclonal Antibodies" (Wiley and Sons, 1991). The antibodies can be used to isolate, identify, characterize or purify the ISLP protein to which it binds. For example, the antibody can be used to detect the ISLP protein in a sample, by allowing antibody and protein to form an immunocomplex, and detecting the presence of the immunocomplex, for example through ELISA or immunoblots.

In a further embodiment of the invention PCR primers and/or probes and kits for detecting the ISLP DNA sequences are provided. PCR primer pairs (wherein each primer is at least 15 to 25, preferably at least 18 or 20 nucleotides in length) to amplify the plant-optimized ISLP DNA of this invention from samples can be synthesized based on the sequence of the ISLP, e.g., the sequence of ISLP1, by methods known in the art (see, e.g., Dieffenbach and Dveksler (1995) *PCR Primer: A Laboratory Manual*, Cold Spring Harbor Laboratory Press; and McPherson at al. (2000) *PCR— Basics: From Background to Bench*, First Edition, Springer Verlag, Germany). Likewise, DNA fragments of the sequence of SEQ ID NO: 1, particularly parts of regions with high homology in several bacterial, preferably bacilli, S-layer proteins, such as the SLH region (Mesnage et al., 2001, Microbiology 147, 1343-1351) such as the SLH region of ISLP1 described above, can be used as hybridization probes. An ISLP detection kit may comprise either ISLP specific primers or ISLP specific probes, and an associated protocol to use the primers or probe to detect ISLP DNA in a sample. For example, such a detection kit may be used to determine, whether a plant has been transformed with a gene encoding an ISLP protein (or part thereof) of the invention.

Because of the degeneracy of the genetic code, some amino acid codons can be replaced by others without changing the amino acid sequence of the protein. Furthermore, some amino acids can be substituted by other equivalent amino acids without changing, or without significantly changing the pesticidal, preferably insecticidal, activity of the protein, or at least without decreasing the pesticidal, preferably insecticidal, activity of the protein. For example, amino acid substitutions include interchanging amino acids within categories:

basic (e.g. Arg, His, Lys), acidic (e.g. Asp, Glu), nonpolar (e.g. Ala, Val, Trp, Leu, Ile, Pro, Met, Phe, Trp, Gly), and polar (e.g. Ser, Thr, Tyr, Cys, Asn, Gln). Such substitutions within categories fall within the scope of the invention as long as the pesticidal activity of the ISLP protein is substantially the same, or not decreased beyond the level needed for obtaining pest control, such as insect control. In addition, non-conservative amino acid substitutions fall within the scope of the invention as long as the pesticidal activity of the ISLP protein is substantially the same, or not decreased. Variants or equivalents of the DNA sequences of the invention include DNA sequences encoding an ISLP as defined herein, hybridizing to the ISLP DNA sequence of SEQ ID NO: 1 under stringent hybridization conditions. Such variants or equivalents should encode a protein with the same or substantially the same pesticidal characteristics as the protein of this invention, while other characteristics such as heat stability or susceptibility to protease cleavage can be altered. In some cases it may be preferred to have available an toxic ISLP with the same or roughly similar toxicity but with a lower heat stability or with higher pepsin sensitivity, and such variants can be made by known processes for random mutagenesis and selection, or by site-directed mutation of an ISLP protein of this invention, e.g., by the introduction of pepsin cleavage sites in an ISLP protein (see, WO 02074799). Variants or equivalents, as used herein, also include DNA sequences having a different codon usage compared to the native ISLP genes of this invention but which encode a protein with the same pesticidal activity and with the same or substantially the same amino acid sequence. The ISLP DNA sequences can be codon-optimized by adapting the codon usage to that most preferred in plant genes, particularly to genes native to the plant genus or species of interest, i.e., into which expression of the ISLP protein is desired using available codon usage tables (e.g., more adapted towards expression in cotton, soybean corn or rice).

For expression in plants or other Eukaryotes, long stretches of AT or GC nucleotides (e.g., stretches of 6 or more A or T nucleotides, or stretches of 6 or more G or C nucleotides) are avoided, removed or reduced in the ISLP genes of the invention, and suitable restriction sites may be introduced.

In addition, the N-terminus of an ISLP protein can be modified to have an optimum translation initiation context, thereby adding or deleting one or more amino acids at the N-terminal of the protein. In most cases, it is preferred that the proteins of the invention to be expressed in plants cells start with a Met-Asp or Met-Ala dipeptide for optimal translation initiation, hence sometimes requiring the insertion in the ISLP DNA of a codon encoding an Asp or Ala amino acid downstream of the start codon as a new second codon (if such second codon is not already Ala or Asp).

The DNA sequences may also be modified to remove illegitimate splice sites or transcription termination signals. As bacterial genes may contain motifs that are recognized in other hosts, especially in eukaryotic host such as plants, as 5' or 3' splice sites or transcription termination signals, transcription in those other hosts may be ineffective or may be terminated prematurely. Illegitimate splice sites or transcription termination signals can be identified by computer-based analysis of the DNA sequences and/or by PCR analysis as known in the art.

Any DNA sequence differing in its codon usage but encoding the same protein or a similar protein with substantially the same pesticidal activity can be constructed, depending on the particular purpose. It has been described in prokaryotic and eukaryotic expression systems that changing the codon usage to that of the host cell has benefits for gene expression in foreign hosts (Bennetzen & Hall, 1982; Itakura et al., 1977). Codon usage tables are available in the literature (Wada et al., 1990; Murray et al., 1989) and in the major DNA sequence databases (e.g. EMBL at Heidelberg, Germany) and as described by Nakamura et al (2000). Accordingly, one of ordinary skill in the art can readily construct synthetic DNA sequences so that the same or substantially the same proteins are produced. It is evident that alternate DNA sequences can be made once the amino acid sequence of the ISLP proteins of this invention is known. Such alternate DNA sequences include synthetic or semi-synthetic DNA sequences that have been changed in order to inactivate certain sites in the gene. This inactivation can be accomplished by, for example, adapting the overall codon usage to that of a more related host organism, such as that of the host organism in which expression is desired. Several techniques for modifying the codon usage to that preferred by the host cells can be found in the patent and scientific literature. The exact method of codon usage modification is not critical for this invention as long as most or all of the cryptic regulatory sequences or processing elements (such as plant polyadenylation signals and splice sites) have been replaced by other sequences, and preferably the AT-content of the coding region approaches that of the host organism.

Small modifications to a DNA sequence such as described above can be routinely made, e.g., by PCR-mediated mutagenesis (Ho et al., 1989, White et al., 1989). More substantial modifications to a DNA sequence can routinely be made by de novo DNA synthesis of a desired coding region using available techniques. The phrase "substantially the same," when used herein, in reference to the amino acid sequence of an ISLP protein, refers to an amino acid sequence that differs no more than 5%, or no more than 2%, from the amino acid sequence of the protein compared to (for the region of the same length, if one protein is smaller). When referring to toxicity of an ISLP protein, the phrase "substantially the same" refers to a protein whose mean LC50 value differs by no more than a factor of 2 to 5, preferably 2, from the mean LC50 value obtained for the protein compared to. In this context, "mean LC50" is the concentration of protein causing 50% mortality of the test population, calculated from three independent bioassays carried out using the same bioassay conditions. LC50 values are calculated with Probit analysis, using the program POLO PC (from LeOra Software, 1987, Berkely, Calif.). It is understood, that 95% (or 90%) confidence limits (an associated parameter calculated with Probit analysis) are calculated for the LC50 values of each of the two proteins to be compared in order to determine whether a statistically significant difference in LC50 values exists. In one embodiment of this invention, the toxicity of the two proteins is seen to be substantially the same, if—in the same or in a comparable experimental setup using proper controls—the confidence limits overlap and substantially different if the confidence limits do not overlap.

The ISLP DNA sequences of the invention, prepared from total DNA, can be ligated in suitable expression vectors and transformed in a bacterial strain, such as *E. coli* or another bacterial strain, preferably in other bacilli such as in *Bacillus thuringiensis*. In one embodiment of the invention, for expression in bacteria, a DNA encoding the bacterial signal peptide of the ISLP protein or a suitable other bacterial signal peptide (e.g., one originating from a secreted protein made by the host cell) is included in the DNA construct. The clones can then be screened by conventional colony immunoprobing methods (French et al., 1986) for expression of the toxin with monoclonal or polyclonal antibodies raised against the ISLP proteins.

The bacterial clones can be screened for production of ISLP proteins (cell lysate or supernatant can be run on SDS-PAGE gels using standard methods and standard western-blotting procedures can be carried out), or the bacteria or purified or semi-purified ISLP protein can be tested for their pesticidal activity compared to control bacteria using methods known in the art or described herein below. The clones can also be analysed for the presence of mRNA encoding ISLP protein using standard PCR procedures, such as RT-PCR.

The genes encoding the ISLP proteins of this invention can be sequenced in a conventional manner (Maxam and Gilbert, 1980; Sanger, 1977) to obtain the DNA sequence.

Sequence comparisons indicate that islp genes are different from previously described genes encoding pesticidal, particularly insecticidal, bacterial toxins, and belong to a new class of genes encoding pesticidal or insecticidal proteins with significant sequence identity to bacterial, preferably bacilli, S-layer proteins.

An pesticidally-effective part of the DNA sequences, encoding a pesticidally-effective portion of the newly identified ISLP proteins, can be made in a conventional manner after sequence analysis of the gene. The amino acid sequence of the ISLP proteins can be determined from the sequence of the isolated DNA. The phrase "a pesticidally effective part (or portion or fragment)" of a DNA sequence encoding the ISLP protein, also referred to herein as a "truncated gene" or "truncated DNA," as used herein refers to a DNA sequence encoding a toxic fragment of an ISLP protein as defined herein.

In order to express all or a pesticidally-effective part of the DNA sequence encoding an ISLP protein of this invention in E. coli, in other bacterial strains, or in plants, suitable restriction sites can be introduced, flanking the DNA sequence. This can be done by site-directed mutagenesis, using well-known procedures (see, e.g., Stanssens et al., 1989; White et al., 1989). In order to obtain improved expression in plants, the codon usage of the ISLP gene or pesticidally effective ISLP gene part of this invention can be modified to form an equivalent, modified or artificial gene or gene part in accordance with PCT publications WO 91/16432 and WO 93/09218 and publications EP 0 385 962, EP 0 359 472 and U.S. Pat. No. 5,689,052. The ISLP genes or gene parts may also be inserted in the plastid (e.g., chloroplast) or mitochondrial genome of a plant and expressed there using a suitable promoter (see, e.g., McBride et al., 1995; U.S. Pat. No. 5,693,507).

For obtaining enhanced expression in monocot plants such as corn or rice, an intron (e.g., a monocot intron) can also be added to the chimeric gene. For example, the insertion of the intron of the maize Adh1 gene into the 5' regulatory region has been shown to enhance expression in maize (Callis et. al., 1987). Likewise, the HSP70 intron, as described in U.S. Pat. No. 5,859,347, may be used to enhance expression. The DNA sequence of the ISLP gene or its toxic fragment can be further changed in a translationally neutral manner. Such changes may modify possibly inhibiting DNA sequences present in the gene part by means of site-directed intron insertion and/or by introducing changes to the codon usage. Changes in codon usage may be, e.g., to adapt the codon usage to that most preferred by plants, particularly the host plant, without changing, or without significantly changing, the encoded amino acid sequence.

In accordance with one embodiment of this invention, the proteins may be targeted to intracellular organelles in plant cells, such as plastids (e.g., chloroplasts), mitochondria, or may be secreted from the cell. For this purpose, in one embodiment of this invention, the chimeric genes of the invention comprise a coding region encoding a signal or targeting peptide, preferably a plant signal or targeting peptide, linked to the ISLP protein-coding region of the invention. Peptides that may be included in the proteins of this invention are the transit peptides for chloroplast or other plastid targeting, such as duplicated transit peptide regions from plant genes whose gene product is targeted to the plastids, the optimized transit peptide of Capellades et al. (U.S. Pat. No. 5,635,618), the transit peptide of ferredoxin-NADP+ oxidoreductase from spinach (Oelmuller et al., 1993), the transit peptide described in Wong et al. (1992) and the targeting peptides in published PCT patent application WO 00/26371. Alternative peptides include those signalling secretion of a protein linked to such peptide, such as the secretion signal of the potato proteinase inhibitor II (Keil et al., 1986), the secretion signal of the alpha-amylase 3 gene of rice (Sutliff et al., 1991) and the secretion signal of tobacco PR1 protein (Cornelissen et al., 1986).

Useful signal peptides in accordance with the invention include the chloroplast transit peptide (e.g., Van Den Broeck et al., 1985), or the optimized chloroplast transit peptide of U.S. Pat. Nos. 5,510,471 and 5,635,618 causing transport of the protein to the chloroplasts, a secretory signal peptide or a peptide targeting the protein to other plastids, mitochondria, the ER, or another organelle. Signal sequences for targeting to intracellular organelles or for secretion outside the plant cell or to the cell wall are found in naturally targeted or secreted proteins, such as those described by Klösgen et al. (1989), Klösgen and Weil (1991), Neuhaus & Rogers (1998), Bih et al. (1999), Morris et al. (1999), Hesse et al. (1989), Tavladoraki et al. (1998), Terashima et al. (1999), Park et al. (1997), Shcherban et al. (1995), all of which are incorporated herein by reference. Alternative signal sequences include the signal peptide sequences from targeted or secreted proteins of corn, cotton, soybean or rice.

To allow secretion of the ISLP proteins to the outside of the transformed host cell, an appropriate secretion signal peptide may be fused to the amino terminal end (N-terminal end) of the ISLP protein. Also, any native bacterial secretion signal peptide can be deleted and replaced by the dipeptide Met-Ala or Met-Asp, or by another signal peptide, such as a plant secretion signal peptide as described above. Particularly, amino acids 1 to 29 of the ISLP proteins of the invention, e.g., the ISLP1 protein shown in SEQ ID NO: 2, comprise a bacterial signal peptide. Amino acids 1 to 29 may be removed, or may be replaced by a Methionine amino acid or by a Met-Ala or Met-Asp dipeptide, or may be replaced by an appropriate signal peptide, such as a plant signal peptide as described above. Signal peptides can be detected using computer based analysis, using programs such as the program Signal Peptide search (SignalP V1.1 or 2.0), using an appropriate matrix (e.g., for prokaryotic gram-positive bacteria) and a threshold score of less than 0.5, a threshold score of 0.25, or less (see, e.g., Von Heijne, Gunnar, 1986 and Bendtsen et al., 2004), or by alignment with similar proteins with known signal peptides.

Furthermore, the binding properties of the ISLP proteins of the invention can be evaluated, using methods known in the art (see, e.g., Van Rie et al., 1990), to determine if the ISLP proteins of the invention bind to sites in the pest, such as the insect gut, that are not recognized (or competed for) by other bacterial proteins. A novel class of insecticidal proteins binding to different binding sites in relevant susceptible insects compared to known insecticidal proteins such as Bt toxins of the Cry, Cyt or VIP toxin families is very valuable. Such proteins can be used to replace known bacterial proteins to which insects may have developed resistance, or to use in combination with insecticidal bacterial proteins having a different mode of action to prevent or delay the development of insect resistance against bacterial proteins, particularly when expressed (preferably simultaneously) in a plant. Because of the characteristics of the ISLP toxins of the present invention, they are extremely useful for transforming plants, e.g., monocots such as corn and rice and dicots such as cotton, vegetable crops, beans and soybean, to protect these plants from insect damage. The mode of action of the ISLP proteins of the current invention is different compared to the known Bt toxins that are currently used in transgenic plant products, such as Cry or VIP proteins of bacilli. Such binding properties can be measured by routine binding assays as described above or in U.S. Pat. Nos. 6,291,156 and 6,137,033.

Especially for insect resistance management purposes for a specific insect pest, it is preferred to combine an ISLP protein of this invention with another insect control protein, particularly a bacterial Cry protein, such as Cry1F, Cry2A or Cry1Ac protein, or a VIP or VIP-like protein, such as VIP3A, preferably a protein which does not recognise at least one binding site recognised by such ISLP protein. Suitable insect control proteins to combine with the ISLP proteins of this invention, particularly for simultaneous expression in plants (such as maize, cotton, *Brassica* species (such as cauliflower or cabbage), rice or soybean plants), include, but are not limited to, the Cry proteins, such as a Cry1B, Cry1C, Cry1D, or Cry1E protein or toxic fragments thereof, a protein comprising the Cry1F toxic fragment or hybrids derived from a Cry1F protein (e.g., the hybrid Cry1A-Cry1F proteins described in U.S. Pat. Nos. 6,326,169; 6,281,016; 6,218,188, or toxic fragments thereof), a protein comprising the Cry1A-type proteins or toxic fragments thereof, preferably the Cry1Ac protein or hybrids derived from the Cry1Ac protein (e.g., the hybrid Cry1Ab-Cry1Ac protein described in U.S. Pat. No. 5,880, 275) or a protein comprising the Cry1Ab protein or insecticidal fragments thereof as described in EP451878, a protein comprising the Cry2Ab protein toxic fragment, such as the Cry2Ab protein-transit peptide fusion protein described in U.S. Pat. No. 6,489,542; a protein comprising the Cry2Ae, Cry2Af or Cry2Ag toxic fragments as described in WO02/057664, a protein comprising the Cry protein toxic fragments as described in WO01/47952, a protein comprising the VIP3Aa protein or a toxic fragment thereof as described in Estruch et al. (1996) and U.S. Pat. No. 6,291,156, insecticidal proteins from *Xenorhabdus* spp. as described in WO98/50427, insecticidal proteins from *Serratia* (particularly from *S. entomophila*) or *Photorhabdus* species strains, such as Tc-proteins from *Photorhabdus* as described in WO98/08932 (e.g., Waterfield et al., 2001; Ffrench-Constant and Bowen, 2000). In one embodiment, such co-expression is easily obtained by transforming a plant already expressing an insect control protein with a DNA encoding an ISLP protein of this invention, or by crossing plants transformed with a known insect control protein with plants transformed with one or more ISLP proteins of this invention. For maize, rice, cotton or soybean plants, the ISLP protein may be used as first insect control protein and as second insect control protein the Cry1Ab, Cry1Ac, Cry2Ae or VIP3Aa proteins or proteins comprising their toxic fragments, hybrids or variants thereof can be used. Methods for obtaining expression of different insecticidal proteins in the same plant in an effort to minimize or prevent resistance development to transgenic insect-resistant plants are described in EP 0 408 403. The different proteins can be expressed in the same plant, or each can be expressed in a single plant and then combined in the same plant by crossing the single plants with one another. For example, in hybrid seed production, each parent plant can express a single protein. Upon crossing the parent plants to produce hybrids, both proteins are combined in the hybrid plant. In some circumstances, it may be preferable to have the different toxin genes inserted at the same place or genetic locus of a plant, so that the genes will not segregate in the progeny of that plant.

It is well known that Bt Cry proteins are expressed as protoxins, which are converted into the toxic core by proteolysis in the insect gut. When combining the ISLP proteins of the invention with Bt Cry proteins, it is understood that cry genes encoding either the full protoxin or the toxic core or any intermediate form may be used.

For selection purposes, and/or for increasing the weed control options, the transgenic plants of the invention may also be transformed with a DNA encoding a protein conferring resistance to a broad-spectrum herbicide, e.g., herbicides based on glufosinate or glyphosate.

The pesticidally effective ISLP gene part or its equivalent, preferably the ISLP chimeric gene, encoding a pesticidally effective portion of the ISLP protein, can be stably inserted in a conventional manner into the nuclear genome of a single plant cell, and the so-transformed plant cell can be used in a conventional manner to produce a transformed plant that controls pests, such as insect pests. In this regard, a T-DNA vector, containing a DNA encoding an ISLP protein, in *Agrobacterium tumefaciens* can be used to transform the plant cell. Thereafter, a transformed plant can be regenerated from the transformed plant cell using the procedures described, for example, in EP 0 116 718, EP 0 270 822, PCT publication WO 84/02913 and published European Patent application EP 0 242 246 and in Gould et al. (1991). The construction of a T-DNA vector for *Agrobacterium*-mediated plant transformation is well known in the art. The T-DNA vector may be either a binary vector as described in EP 0 120 561 and EP 0 120 515 or a co-integrate vector which can integrate into the *Agrobacterium* Ti-plasmid by homologous recombination, as described in EP 0 116 718. Preferred T-DNA vectors each contain a promoter operably linked to the pesticidally effective ISLP gene part between T-DNA border sequences, or at least located to the left of the right border sequence. Border sequences are described in Gielen et al. (1984). Other types of vectors can be used to transform the plant cell, using procedures such as direct gene transfer (as described, for example in EP 0 223 247), pollen mediated transformation (as described, for example in EP 0 270 356 and WO 85/01856), protoplast transformation as, for example, described in U.S. Pat. No. 4,684,611, plant RNA virus-mediated transformation (as described, for example in EP 0 067 553 and U.S. Pat. No. 4,407,956), liposome-mediated transformation (as described, for example in U.S. Pat. No. 4,536,475), and other methods, such as the recently described methods for transforming certain lines of corn (e.g., U.S. Pat. No. 6,140,553; Fromm et al., 1990; Gordon-Kamm et al., 1990) and rice (Shimamoto et al., 1989; Datta et al. 1990) and the method for transforming monocots generally (PCT publication WO 92/09696). A suitable method for cotton transformation is described in PCT patent publication WO 00/71733. For rice transformation, reference is made to the methods described in WO92/09696, WO94/00977 and WO95/06722.

The terms “maize” and “corn” are used herein synonymously, referring to *Zea mays*. Cotton as used herein refers to *Gossypium* spp., particularly *G. hirsutum* and *G. barbadense*. The term “rice” refers to *Oryza* spp., particularly *O. sativa*. “Soybean” refers to *Glycine* spp, particularly *G. max*. Vegetable plants or vegetables, as used herein, refers to cucumber, tomato, lettuce, Brussels endive, *Brassica* vegetables such as cauliflower or cabbages, leek, lettuce, onion, (water) melon, artichoke, carrot, or peppers.

Besides transformation of the nuclear genome, also transformation of the plastid genome (e.g., the chloroplast genome) is included in the invention, Kota et al. (1999) have described a method to over-express a Cry2Aa protein in tobacco chloroplasts.

The resulting transformed plant can be used in a conventional plant breeding scheme to produce more transformed plants with the same characteristics or to introduce the pesticidally effective ISLP gene part into other varieties of the same or related plant species. Seeds, which are obtained from the transformed plants, contain the gene encoding the ISLP protein as a stable genomic insert. Cells of the transformed plant can be cultured in a conventional manner to produce the pesticidally effective portion of the ISLP toxin or protein, which can be recovered for use in conventional insecticide compositions, particularly insecticide compositions against Lepidoptera.

The pesticidally effective ISLP gene part is inserted in a plant cell genome so that the inserted gene is downstream (i.e., 3') of, and under the control of, a promoter which can direct the expression of the gene part in the plant cell. This may be accomplished by inserting the ISLP chimeric gene in the plant cell genome, for example in the nuclear or plastid (e.g., chloroplast) genome.

Suitable promoters include, but are not limited to: the strong constitutive 35S promoters (the "35S promoters") of the cauliflower mosaic virus (CaMV) of isolates CM 1841 (Gardner et al., 1981), CabbB-S (Franck et al., 1980) and CabbB-JI (Hull and Howell, 1987); the 35S promoter described by Odell et al. (1985), promoters from the ubiquitin family (e.g., the maize ubiquitin promoter of Christensen et al., 1992, EP 0 342 926, see also Cornejo et al., 1993), the gos2 promoter (de Pater et al., 1992), the emu promoter (Last et al., 1990), Arabidopsis actin promoters such as the promoter described by An et al. (1996), rice actin promoters such as the promoter described by Zhang et al. (1991) and the promoter described in U.S. Pat. No. 5,641,876; promoters of the Cassava vein mosaic virus (WO 97/48819, Verdaguer et al. (1998)), the pPLEX series of promoters from Subterranean Clover Stunt Virus (WO 96/06932, particularly the S7 promoter), a alcohol dehydrogenase promoter, e.g., pAdh1S (GenBank accession numbers X04049, X00581), and the TR1' promoter and the TR2' promoter (the "TR1' promoter" and "TR2' promoter", respectively) which drive the expression of the 1' and 2' genes, respectively, of the T-DNA (Velten et al., 1984). Alternatively, a promoter can be utilized which is not constitutive but rather is specific for one or more tissues or organs of the plant (e.g., leaves and/or roots) whereby the inserted ISLP gene part is expressed only in cells of the specific tissue(s) or organ(s). For example, an insecticidally effective ISLP gene part could be selectively expressed in the leaves of a plant (e.g., corn, cotton, rice, soybean) by placing the insecticidally effective gene part under the control of a light-inducible promoter such as the promoter of the ribulose-1,5-bisphosphate carboxylase small subunit gene of the plant itself or of another plant, such as pea, as disclosed in U.S. Pat. No. 5,254,799. The promoter can, for example, be chosen so that the ISLP gene of the invention is only expressed in those tissues or cells on which the target pest, such as an insect pest, feeds so that feeding by the susceptible target pest will result in reduced damage to the host plant, compared to plants which do not express the ISLP gene. A pest mainly damaging the roots can thus effectively be controlled by expressing an ISLP gene under a root specific promoter. A promoter preferentially active in roots is described in WO00/29566. A suitable promoter for root preferential expression is the ZRP promoter (and modifications thereof) as described in U.S. Pat. No. 5,633,363. Another alternative is to use a promoter whose expression is inducible, for example a wound-inducible promoter such as, e.g., the MPI promoter described by Cordera et al. (1994), which is induced by wounding (such as caused by insect feeding), or a promoter inducible by a chemical, such as dexamethasone as described by Aoyama and Chua (1997) or a promoter inducible by temperature, such as the heat shock promoter described in U.S. Pat. No. 5,447,858, or a promoter inducible by other external stimuli. In monocot plants, such as corn and rice, the Agrobacterium TR2' promoter, or variants thereof, are a preferred wound-induced promoter to drive transcription of a chimeric ISLP gene of the invention, see WO 03/093483.

The pesticidally effective ISLP gene part may be inserted into the plant genome so that the inserted gene part is upstream (i.e., 5') of suitable 3' end transcription regulation signals (i.e., transcript formation and polyadenylation signals). This is preferably accomplished by inserting the ISLP chimeric gene in the plant cell genome. Suitable polyadenylation and transcript formation signals include those of the CaMV 35S gene, the nopaline synthase gene (Depicker et al., 1982), the octopine synthase gene (Gielen et al., 1984) and the T-DNA gene 7 (Velten and Schell, 1985), which act as 3'-untranslated DNA sequences in transformed plant cells.

Introduction of the T-DNA vector into Agrobacterium can be carried out using known methods, such as electroporation or triparental mating.

The pesticidally-effective ISLP gene part can optionally be inserted in the plant genome as a hybrid gene (U.S. Pat. No. 5,254,799; Vaeck et al., 1987) under the control of the same promoter as a selectable or scorable marker gene, such as the neo gene (EP 0 242 236) encoding kanamycin resistance, so that the plant expresses a fusion protein that is easily detectable.

Transformation of plant cells can also be used to produce the proteins of the invention in large amounts in plant cell cultures, e.g., to produce an ISLP protein that can then be applied onto crops after proper formulation. When reference to a transgenic plant cell is made herein, this refers to a plant cell (or also a plant protoplast) as such in isolation or in tissue culture, or to a plant cell (or protoplast) contained in a plant or in a differentiated organ or tissue, and both possibilities are specifically included herein. Hence, a reference to a plant cell in the description or claims is meant to refer not only to isolated cells in culture, but also to any plant cell, wherever it may be located or in whatever type of plant tissue or organ it may be present.

All or part of an ISLP gene, encoding an insecticidal, particularly anti-Lepidopteran, protein, can also be used to transform other microorganisms, including bacteria, such as a B. thuringiensis, which may already have insecticidal activity against Lepidoptera or Coleoptera. Thereby, a transformed Bt strain can be produced which is useful for combating a wide spectrum of Lepidopteran and/or Coleopteran insect pests or for combating additional Lepidopteran insect pests. Transformation of bacteria, such as bacteria of the genus Pseudomonas, Agrobacterium, Bacillus or Escherichia, with all or part of the ISLP gene of this invention, incorporated in a suitable cloning vehicle, can be carried out in a conventional manner, using, e.g., conventional electroporation techniques as described in Mahillon et al. (1989) and in PCT Patent publication WO 90/06999.

Transformed Bacillus species strains containing the ISLP gene of this invention can be fermented by conventional methods (Dulmage, 1981; Bernhard and Utz, 1993) to provide high yields of cells. Under appropriate growth conditions, these strains can produce ISLP protein in high yields.

Alternative suitable host microorganisms in which the ISLP genes can be expressed are fungi, algae, or viruses, particularly species which are plant colonizing (e.g., (endo) symbiontic) species or pathogens of pests, such as insect pests.

An insecticidal, particularly anti-Lepidopteran, composition of this invention can be formulated in a conventional manner using the microorganisms transformed with the ISLP gene, or an ISLP protein, or an insecticidally effective ISLP portion as an active ingredient, together with suitable carriers, diluents, emulsifiers and/or dispersants (e.g., as described by Bernhard and Utz, 1993). This insecticide composition can be formulated as a wettable powder, pellets, granules or dust or as a liquid formulation with aqueous or non-aqueous solvents as a foam, gel, suspension, concentrate, etc. Examples of compositions comprising insecticidal bacterial spores are described in WO96/10083.

A method for controlling insects, particularly *Lepidoptera* or *Coleoptera*, in accordance with this invention can comprise applying (e.g., spraying), to a locus (area) to be protected, an insecticidal amount of the ISLP proteins or compositions comprising the ISLP proteins or comprising host cells transformed with the ISLP genes of this invention. The locus to be protected can include, for example, the habitat of the insect pests or growing vegetation (e.g. application to the foliage) or an area where vegetation is to be grown (e.g. application to soil or water). In one embodiment, a composition according to the present invention comprises an insecticidal amount of at least one of the ISLP proteins of the invention, which may be produced by a bacterial host. Such a composition may be applied to leaves, soil, or seed coating.

The term "contacting" is used herein to mean, "to bring into physical contact with." Contacting a plant with an insecticidal protein means that the insecticidal protein is brought into contact with cells of the plant, either internally (for example by expression in the plant) or externally (for example by applying compositions comprising the insecticidal protein externally to the plant). It is understood that the term does not indicate the length of time of contact, but comprises any period of contact. When referring to a method of protecting a plant against insect damage comprising contacting said plant (or cells or tissues thereof) with an insecticidal protein of the invention, the contact may be long enough and extensive enough (with a high enough amount of protein contacting a large enough number of cells) to prevent or reduce insect damage.

This invention further relates to a method for controlling Lepidopteran or Coleopteran cotton pests or sucking insect pests of cotton, such as boll weevils, bollworms, budworms, or earworms, *Aphis gossypii, Myzus persicae, Lygus* bugs, whitefly, stink bugs, thrips, or Creontiades dilutus. Specific Lepidopteran cotton pests that may be controlled by the methods of the present invention include, but are not limited to, those selected from the group of *Helicoverpa zea* (Corn Earworm), *Helicoverpa armigera* (Cotton Bollworm), *Helicoverpa punctigera* (Native Bollworm), *Heliothis virescens* (Tobacco Budworm), *Spodoptera frugiperda* (Fall Armyworm) and *Pectinophora gossypiella* (Pink Bollworm). The method of controlling cotton insect pests comprises applying to an area or plant to be protected, an ISLP protein as defined herein. This may be accomplished by contacting a cotton plant with an ISLP protein of this invention, for example by planting a plant, such as a cotton plant, transformed with an ISLP gene of this invention, or spraying a composition containing an ISLP protein of this invention. The invention also relates to the use of the ISLP proteins of this invention, against Lepidopteran, aphid or Coleopteran cotton insect pests to minimize damage to cotton plants.

A target insect pest for the ISLP proteins of this invention, such as the ISLP1 protein, can also be *Epilachna varivestis*, the Mexican bean beetle. This is a serious pest in various legume crops in North America, but is also a serious problem in other crops in Asia and Africa as cucurbits, solanaceae, beans, maize, sorghum, rice, wheat, cotton, sesame, lettuce, soybean and cowpea.

This invention further relates to a method for controlling Lepidopteran or Coleopteran maize pests or aphids, such as corn leaf aphids (*Rhopalosiphum maidis*), greenbugs (*Schizaphis graminum*) or green peach aphids (*Myzus persicae*); earworms, armyworms, cutworms, stalkborers, wireworms, corn borers or corn rootworms. Specific maize pests that may be controlled by the methods of the present invention may be selected from the group of *Helicoverpa zea* (Corn Earworm), *Agrotis ipsilon* (Black Cutworm), *Ostrinia nubilalis* (European Corn Borer), *Diabrotica* spp. corn rootworms and *Spodoptera frugiperda* (Fall Armyworm). The method comprises applying to an area or plant to be protected, an ISLP protein as defined herein, as defined herein. This may be accomplished by contacting a maize plant with an ISLP protein of this invention, for example by planting a maize plant transformed with an, ISLP gene of this invention, or spraying a composition containing an ISLP protein of this invention. The invention also relates to the use of the ISLP proteins of this invention, against Lepidopteran maize insect pests to minimize damage to maize plants.

This invention further relates to a method for controlling Lepidopteran or Coleopteran rice pests or sucking insects on rice, such as rice leafhoppers or planthoppers, rice (black) bugs, rice stemborers, rice skippers, rice cutworms, rice armyworms, rice caseworms, and rice leaffolders or white grubs. Specific Lepidopteran rice insect pests that may be controlled by the methods of the present invention may be selected from the group of Yellow Stem Borer (*Scirphophaga incertulas*), Leaffolder (*Cnaphalocrocis medinalis*), Pink Stem Borer (*Sesamia inferens*) and Corn Spotted Stem Borer (*Chilo partellus*). The method comprises applying to an area or plant to be protected, an ISLP protein as defined herein. This may be accomplished by contacting a rice plant with an ISLP protein of this invention, for example by planting a rice plant transformed with an ISLP gene of this invention, or spraying a composition containing an ISLP protein of this invention. The invention also relates to the use of the ISLP proteins of this invention, against Lepidopteran, aphid or Coleopteran rice insect pests to minimize damage to rice plants.

This invention further relates to a method for controlling Lepidopteran, aphid or Coleopteran soybean pests. Specific soybean pests that may be controlled by the methods of the present invention may be selected from the group of Velvet Bean Caterpillar (*Anticarsia gemmatalis*), Soybean Looper (*Pseudoplusia includens*), Beet Armyworm (*Spodoptera exigua*), Yellowstriped Armyworm (*Spodoptera omithogalli*), Corn Earworm (*Helicoverpa zea*), Pod Borer (*Epinotia aporema*) and *Rachiplusia nu*. This method comprises applying to an area or plant to be protected, an ISLP protein as defined herein. This may be accomplished by contacting a soybean plant with an ISLP protein, e.g. an ISLP1 protein, of this invention, for example by planting a soybean plant transformed with an ISLP gene of this invention, or spraying a composition containing an ISLP protein of this invention. The invention also relates to the use of the ISLP proteins of this invention, against Lepidopteran soybean insect pests to minimize damage to soybean plants.

To obtain the ISLP toxin or protein, cells of the recombinant hosts expressing the ISLP protein can be grown in a conventional manner on a suitable culture medium. The produced ISLP protein can be separated and purified from lysed cells, or when secreted, from the growth medium. If the proteins are not secreted, the cells can be lysed using conventional means such as enzyme degradation, by sonication or by using detergents or the like. The ISLP protein can then be separated and purified by standard techniques such as chromatography, extraction, electrophoresis, or the like.

The term "gene" as used herein means any DNA or RNA fragment comprising a region (the "transcribed region") which may be transcribed into an RNA molecule (e.g., an mRNA) in a cell, operably linked to suitable regulatory regions, e.g., a plant-expressible promoter. A gene may thus comprise several operably linked fragments such as a promoter, a 5' leader sequence, a coding region, and a 3' nontranslated sequence, comprising a polyadenylation site. A gene endogenous to a particular organism (such as a plant species or a bacterial strain) is a gene, which is naturally found in that organism in nature. A "chimeric gene," when referring to an ISLP DNA of this invention, refers to an ISLP DNA sequence having 5' and/or 3' regulatory sequences different from the naturally-occurring bacterial 5' and/or 3' regulatory sequences, which drive the expression of the ISLP gene in its native host cell.

The term "expression of a gene" when referring to the ISLP genes of the invention, refers to the process wherein a DNA coding region which is operably linked to appropriate regulatory regions, such as to a promoter, is transcribed and translated into a protein.

For the purpose of this invention the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other is regarded as a position with non-identical residues (for sequences of different length the size is equaled to that the shortest sequence, e.g., in the case of the alignment of a fragment of an ISLP and a full length S-layer protein, the comparison is with respect to the corresponding part of the same size in the S-layer protein). To calculate sequence identity between two sequences for the purpose of this invention, the GAP program, which uses the Needleman and Wunsch algorithm (1970) and which is provided by the Wisconsin Package, Version 10.2, Genetics Computer Group (GCG), 575 Science Drive, Madison, Wis. 53711, USA, may be used. The GAP parameters used are a gap creation penalty=50 (nucleotides)/8 (amino acids), a gap extension penalty=3 (nucleotides)/2 (amino acids), and a scoring matrix "nwsgapdna" (nucleotides) or "blosum62" (amino acids). GAP uses the Needleman and Wunsch global alignment algorithm to align two sequences over their entire length, maximizing the number of matches and minimizes the number of gaps. The default parameters are a gap creation penalty=50 (nucleotides)/8 (proteins) and gap extension penalty=3 (nucleotides)/2 (proteins). For nucleotides, the default scoring matrix used is "nwsgapdna" and for proteins the default scoring matrix is "blosum62" (Henikoff & Henikoff, 1992). Similarly, the percentage sequence similarity can be obtained in such alignments using standard software, which indicates not only the percentage of identical residues but also includes residues which differ but are of similar nature (such as differences in conservative amino acids, as defined herein, for protein alignments). Examples of algorithms that are suitable for determining percent sequence identity and sequence similarity are the BLAST and BLAST 2.0 algorithms, which are described in Altschul et al. (1977) and Altschul et al. (1990).

These and/or other embodiments of this invention are reflected in the claims, which form part of the description of the invention.

The following Examples illustrate the invention, and are not provided to limit the invention or the protection sought. The sequence listing referred to in the Examples, the Claims and the Description is as follows:

SEQ ID NO: 1: DNA coding sequence and amino acid sequence of the islp1 gene
SEQ ID NO: 2: amino acid sequence of the ISLP1 protein
SEQ ID NO: 3: PCR primer ISLP1Xder
SEQ ID NO: 4: PCR primer ISLP1Xrev
SEQ ID NO: 5: PCR primer BSLX-1
SEQ ID NO: 6: PCR primer BSLX-4
SEQ ID NO: 7: PCR primer BSLX-3
SEQ ID NO: 8: PCR primer BSLX-2
SEQ ID NO: 9: PCR primer BSLN-5
SEQ ID NO:10: PCR primer BSLN-6
SEQ ID NO:11: PCR primer BSLP-8
SEQ ID NO:12: PCR primer BSLP-7
SEQ ID NO:13: PCR primer EAGB-4
SEQ ID NO:14: amino acid sequence of the N-terminus of the isolated mature ISLP1 protein
SEQ ID NO:15: amino acid sequence of the N-terminus of the about 50 kDa tryptic fragment of the ISLP1 protein Unless stated otherwise in the Examples, all recombinant DNA techniques are carried out according to standard protocols as described in Sambrook and Russell (2001) *Molecular Cloning: A Laboratory Manual*, Third Edition, Cold Spring Harbor Laboratory Press, NY, in Volumes 1 and 2 of Ausubel et al. (1994) *Current Protocols in Molecular Biology, Current Protocols*, USA and in Volumes I and II of Brown (1998) *Molecular Biology LabFax*, Second Edition, Academic Press (UK). Standard materials and methods for plant molecular work are described in *Plant Molecular Biology Labfax* (1993) by R. D. D. Croy, jointly published by BIOS Scientific Publications Ltd (UK) and Blackwell Scientific Publications, UK. Standard materials and methods for polymerase chain reactions can be found in Dieffenbach and Dveksler (1995) *PCR Primer: A Laboratory Manual*, Cold Spring Harbor Laboratory Press, and in McPherson at al. (2000) *PCR—Basics: From Background to Bench*, First Edition, Springer Verlag, Germany.

It should be understood that the preceding is merely a detailed description of particular embodiments of this invention and that numerous changes to the disclosed embodiments can be made in accordance with the disclosure herein without departing from the spirit or scope of the invention. The preceding description, therefore, is not meant to limit the scope of the invention. Rather, the scope of the invention is to be determined only by the appended claims and their equivalents.

EXAMPLES

Materials and Methods

Bacterial strains. *Bacillus thuringiensis* (Bt) strains were isolated from dead insect (*Epilachna varivestis*) samples by the acetate selection method (Travers et al., 1987). The *E. varivestis* dead bodies were washed twice with sodium hypochlorite 1% and with sterile water before homogenization and Bt strain isolation.

Bioassays. The bioassays against *E. varivestis* were performed with spore/crystal suspensions using the leaf-dip technique. Plant leaves of *Phaseolus vulgaris* were dipped in toxin dilution and allowed to dry. Different protein concentrations were tested with five larvae of the first instar per treated leaf. Four repetitions were done per concentration. Mortality and leaf damage was determined after 6 days. Bioassays against first instar larvae of *Manduca sexta* or *Spodoptera frugiperda* were done in artificial diet as previously described (Bravo et al., 1998). Bioassays against *Aedes aegypti* mosquitoe larvae were done in 100 ml H2O as described by Ibarra et al. (2003).

Purification of the crystal inclusion present in ISLP1 strain. The ISLP1 strain was grown in Petri dishes containing solid nutrient broth sporulation medium (Lereclus et al., 1995). The spore/crystal mixture was collected in 5 ml sterile water. Centrifuged 10 min at 10,000 rpm, the supernatant was recovered and the pellet containing only spores was discarded. This step was repeated 5 times in order to eliminate all spores from the suspension. Finally the crystal inclusions were recovered by centrifugation for 30 min at 19,000 rpm. The crystal proteins were solubilized in 50 mM Na2CO3, pH 10.5 0.2% beta-mercaptoethanol and purified by anion exchange chromatography in a Q-sepharose column FPLC Pharmacia (Hill, 1983).

N-Terminal sequencing. N-terminal sequencing of the protein produced by the ISLP1 strain was performed at the Harvard Microchemistry Facility of Harvard University (Cambridge, Mass.) after SDS-PAGE 7% and transfer onto polyvinylidene difluoride membranes (Millipore Co., Bedford, Mass.) in a semidry transfer chamber as directed by the manufacturer. The N-terminal sequence was also done from a trypsin fragment of the ISLP1 crystal protein that was purified by HPLC size exclusion chromatography (Güereca and Bravo, 1999).

Immunization of rabbits. A New Zealand white rabbit was immunized with the ISLP1 protein by subcutaneous injections. 1 mg of the ISLP1 protein in PBS was emulsified with Freund's complete adjuvant and injected at five sites on the back of the rabbit. The rabbit was boosted three times with 1 mg of the ISLP1 protein, mixed with incomplete adjuvant, at 15 days intervals. A sample of the blood was isolated 40 days after the primary immunization.

Determination of the DNA sequence of the ISLP1 gene. Based on the N-terminal sequence of the ISLP1 protein, two PCR primers, ISLP1Xder (ACGCTCTAGATAGCAGG-TAAATCATTCCCAGACG, SEQ ID NO. 3) and ISLP1Xrev (ACGCTCTAGATCGCCGTATTGGTCAGTTGTTAC, SEQ ID NO.4), were designed amplifying a 1536 bp PCR product. PCR reactions were performed by standard techniques (Sambrook et al., 1989) with Pfu DNA polymerase (Stratagene La Jolla, Calif.) because of its high fidelity. Total DNA was extracted from ISLP1 strain (Msadek et al., 1990) and used as template in all PCR reactions. The PCR product was used for Blast analysis and two related sequences of S-layer genes were obtained (accession number u38842 and x99724). Alignment of these sequences demonstrated that they shared similar 5' and 3' ends. Four PCR primers were designed from 5' and 3' terminal ends of these 3-layer genes and from the internal sequence of the ISLP1-amplified fragment. Primers BSLX-1 (GCTCTAGATGAGAGTGCTT-TATAGGAAAAT, SEQ ID NO: 5) and BSLX-4 (GCTCTA-GATCTTCAGCCGGAGCGTATGTACC, SEQ ID NO: 6) amplify a 553 bp 5' end fragment, and primers BSLX-3 (GCTCTAGATACTGCTGAGGCTGCTGGTGAGG, SEQ ID NO: 7) and BSLX-2 (GCTCTAGATCCTCGACCTGCT-TCACTATCA, SEQ ID NO: 8) amplify a 1372 bp 3' fragment. Each PCR fragment was digested with Xba1 (New England BioLabs, Beverly, Mass.) and cloned into pBluescript SK (Stratagene, La Jolla, Calif.) previously digested with Xba1. The ligation products were purified by extraction with phenol/chloroform, precipitated with ethanol and electroporated into TG1 *Escherichia coli* electrocompetent cells (Lereclus et al., 1989). Transformant colonies were grown on LB agar plates, supplemented with ampicillin (100 □g/ml), colonies were mixed with glycerol (20%) and stored at −70° C. These plasmids named ISLP1-SL1, ISLP1-SL2 and ISLP1-SL3 and their DNA inserts were sequenced using automatic DNA sequencing facilities.

Cloning and expression of ISLP1 protein in *B. thuringiensis*. The complete *islp*1 gene was reconstituted by cloning three PCR fragments into plasmid pHT315 (Lereclus et al., 1989). The first PCR product containing the promotor region was obtained with primers BSLX-1 and BSLN-5 (TCTTTGCCATGGTATAAATTTCCTCCTTC, SEQ ID NO: 9). Primer BSLX-1 has an extra 10 bp at the 5' end containing a Xba1 restriction site and primer BSLN-5 has an internal Nco1 restriction site. The second PCR fragment was obtained with primer BSLN-6 (TTATACCATGGCAAA-GACTAACTCTTAC, SEQ ID NO:10) that contains an internal Nco1 restriction site and primer BSLP-8 (AAAACTG-CAGAAGTACCGTCAGCACTTGCTTC, SEQ ID NO:11) that includes the unique Pst1 restriction site of the islp1 gene. Finally, the third PCR fragment was amplified with primer BSLP-7 (AACGCTGCAGTTGTAACACTTGGTGG-TAAAG, SEQ ID NO: 12) that also includes the unique Pst1 restriction site and primer EAGB-4 (CGGGATCCTCCTC-GACCTGCGTCACTATCA, SEQ ID NO: 13) that is similar to BSLX-2 but has 8 extra by containing a BamHI restriction site at the 5' end. Each PCR product was purified and digested with the corresponding restriction enzymes, and subcloned separately into pBluescript KS. The DNA fragments contained in these plasmids were purified, ligated and inserted into plasmid pHT315 previously digested with Xba1 and BamHI. The product of the ligation reaction was directly transformed in the acrystalliferous *Bacillus thuringiensis* strain 407 (Lereclus et al., 1989) that was kindly provided by Dr. Didier Lereclus (Pasteur Institute, France) and was grown at 30° C. in LB supplemented with 7.5 □g/ml erythromycin. The resulting plasmid was named pHT-ISLP1. The Bt strain containing pHT-ISLP1 was grown in Petri dishes containing solid HCT medium supplemented with erythromycin. The spore/crystal mixture was collected in 2 ml sterile water and used in Western blot experiments. Detection was done with anti-SL-ISLP1 polyclonal antibody (1/10,000; 1 h) and visualized with a goat anti-rabbit antibody coupled with horseradish peroxidase (HR) (Sigma, St. Louis, Mo.) (1/7,500; 1 h), followed by SuperSignal chemiluminescent substrate (Pierce, Rockford, Ill.) as described by the manufacturer.

Chemical Extraction of S-layer Protein

The ISLP1 strain, the Bt strain containing pHT-ISLP1 and the acrystalliferous Bt strain 407 were grown in BHI (Difco) broth medium until 0.9 O.D. at 600 nm in order to have exclusively vegetative cells. Cells were pelleted by centrifugation (10 min at 10,000 rpm). Pellets were washed and resuspended in ⅟50 of the initial volume of 1, 1.5 or 2 M guanidinium hydrochloride (pH 2.5), as described by Luckevich and Beveridge (1989) to extract specifically the cell-surface-anchored proteins. The samples were centrifuged 10 min at 10,000 rpm, the pellets containing the bacterial cells and the supernatants containing the extracted proteins were then precipitated by adding trichloroacetic acid (TCA) to a final concentration of 10% (20 min at −20° C.), centrifuged 10 min at 10,000 rpm, washed two times with water and suspended in 0.03 N NaOH. An equal volume of Laemmli sample loading buffer 2× was added. Samples were boiled for 5 min and loaded in two 10% SDS-PAGE gels. One gel was stained with Coomassie brilliant blue and the duplicated gel was electrotransferred into polyvinylidene difluoride (PVDF) Immobilon membranes (Amersham Biosciences) for Western Blot detection using anti-SL-ISLP1 polyclonal antibody as described above.

Results

Isolation of Bt strains active against *Epilachna varivestis*. Four Bt strains isolated in Mexico from dead bodies of *E. varivestis* were used in toxicity assays against *E. varivestis* larvae (Coleoptera:Coccinellidae). These strains were very similar since all of them produced a similar crystal composed of a 100 kDa protein and had identical total protein pattern. The four strains showed 100% mortality to *E. varivestis* larvae when tested at 100 and 1000 ng/cm2. We selected one of these strains, named ISLP1, and purified the crystal inclusion by successive centrifugation as described in the Materials and Methods, followed by anion exchange chromatography. The bioassays against *E. varivestis* larvae performed with spore/crystal mixture of this strain showed a lethal concentration (LC50) of 16 ng/cm2 (7-25 of 95% confidential limits). With pure crystal protein an LC50 of 8.6 ng/cm2 (4-14 of 95% confidential limits) was found. The pure crystal or the spore/crystal mixture (up to 10,000 ng/cm2) showed no toxic activity against first instar larvae of the lepidopteran insects *Manduca sexta* or *Spodoptera frugiperda*, and no toxicity was found against 4th instar larvae of the dipteran *Aedes aegypti*.

The ISLP1 strain was characterized by PCR reactions using general and specific primers for cry1, cry3, cry5, cry7, cry8, cry9, cry11, cry13, cry14, and cyt1A genes (Bravo et al., 1998; Ceron et al., 1994; Ceron et al., 1995). All PCR reactions were negative. The 16S RNAr gene of the ISLP1 strain was then amplified using the primers designed by Aguino de Muro and Priest (Aguino de Muro and Priest, 1993). Blast analysis of the 16S DNA sequence confirmed that the ISLP1 strain belongs to the *Bacillus thuringiensis* group.

Characterization of the ISLP1 Protein Found in Crystal Inclusions

The 100 kDa protein produced by the ISLP1 strain was purified by anion exchange chromatography, transferred to Immobilon PSQ, and the amino-terminal sequence of the protein was obtained. This amino acid sequence (AGKSFP-DVPAGH, SEQ ID NO: 14) corresponds to the first 12 amino acids after the leader-peptide of an S-layer protein precursor from *B. licheniformis* OlpA (GenBank accession number U38842, GenPept accession number AAC44405) and *B. anthracis* EA1 (GenBank accession number X99724, GenPept accession number CAA68063). A trypsin digestion of the pure ISLP1 protein was performed and a fragment of about 50 kDa was purified by HPLC size exclusion chromatography. An internal sequence of 18 amino acids was obtained that was also found in Olp1 and EA1 S-layer proteins: KLPVTFVTTDQYGDPYGAN (SEQ ID NO: 15).

PCR primers (ISLP1Xder and ISLP1Xrev) were designed from the two obtained N-terminal sequences of this protein and used for amplification of an internal fragment that was DNA sequenced. Blast analysis of the resulting sequence showed a high score with sequences of two S-layer genes olpA and eag (GenBank accession numbers u38842 and x99724). Using this information and the DNA sequence alignment of these genes, novel PCR primers were designed to amplify two other overlapping PCR-products. One includes 500 bp upstream of the ATG codon in order to have the putative promoter, and the other included 200 bp after the putative stop codon. The sequence of the complete islp1 gene was obtained (SEQ ID NO: 1). The open reading frame (ORF) found in this sequence contained 2,589 nucleotides, it was preceded by a Shine-Dalgarno sequence. A palindromic structure was observed 22 nucleotides downstream from the stop codon. The comparison of the N-terminus of the sequenced protein and of the amino acid sequence deduced from the nucleotide sequence confirmed that this protein is also synthesized as a pre-polypeptide with a 29 amino acid signal peptide. The N-terminus of the mature protein with signal sequence removed is at amino acid position 30 in SEQ ID NO: 2. Three S-Layer homology motifs (SLH) are present in the protein sequence, the first was observed between in the region of amino acid position 34 to 76, the second in the region of amino acid position 95-136, and the third in the region of amino acid position 162-198 (all are amino acid positions in SEQ ID NO: 2).

Finally, the complete islp1 gene was cloned directly into acrystalliferous *B. thuringiensis* strain 407, by amplifying three PCR fragments that overlap in a NcoI and a Pst1 restriction site, respectively, as described in the Materials and Methods. It was not possible to obtain *E. coli* transformants with this construct. Other authors found that in many cases the cloning of the S-layer gene in *E. coli* with its regulatory region could lead to problems (Mesnage et al., 2001; Sun et al., 2001). The resulting Bt strain expressed the ISLP1 protein as judged by immunodetection of the protein using a polyclonal antibody raised against the pure ISLP1 protein. A sporulated culture of this strain showed 100% mortality of *E. varivestis* larvae when assayed at 100 and 1000 ng/cm2 in contrast with the control strain transformed with the pHT315 shuttle vector that does not express the ISLP1 protein and did not show any toxicity to *E. varivestis* larvae.

Expression of ISLP1 in the ISLP1 Strain

We analysed the expression of the ISLP1 protein during growth in SP sporulation medium. This protein is expressed during the vegetative and the sporulation phase of growth. During vegetative phase of growth the protein was associated to the bacteria since all the protein detected by Western blot was found in the bacterial pellet obtained after centrifugation of the culture. However, during the sporulation phase the ISLP1 protein was also found in the supernatant of centrifuged cultures.

Luckevich and Beveridge (1989) described a specific extraction procedure for the S-Layer protein of *B. thuringiensis* subsp. *galleria*. We used this method to test whether the ISLP1 protein has the ability to bind to the cell surface from the original strain and in the transformant strain. Treatment of vegetative cells with 2 M chaotropic agent at low pH resulted in the specific extraction of the SL-ISLP1 protein as judged by the SDS-PAGE and the Western Blot analysis of the extracted protein. The SL-ISLP1 protein was only present in the ISLP1 strain and the Bt-transformant strain, this protein was absent in the 407 acrystalliferous strain. Similarly as reported by Luckevich and Beveridge (1989), the ISLP1 protein was extracted only with the treatment of 2 M chaotropic reagent, treatments with lower concentrations of chaotropic reagent (1-1.5 M) did not extract the protein from the bacteria cells.

Western blot detection of this protein was also done in other Bt strains as Bt subs kurstaki HD1 and HD73, Bt subs israelinsis HD567, Bt subs aizawai HD137, Bt subs tolworthi HD125, Bt subs morrisoni tenebrionis, showing that this protein is not produced by these strains. PCR analysis of these strains, using primers ISLP1Xder and ISLP1Xrev, also confirmed that these Bt strains do not harbour the ISLP1 coding sequence.

The ISLP1 protein (SEQ ID NO: 2) has high sequence identity to the EA1 S-layer protein from *Bacillus anthracis* (92% sequence identity for the protein including the signal peptide) and to the CTC2 protein reported in *B. thuringiensis* (89% sequence identity for the protein including the signal peptide). The amino acid sequence identity of the ISLP1 protein to the other *B. anthracis* S-layer protein SAP is only 32%.

REFERENCES

Aguino de Muro and Priest. (1993) FEMS Microbiol Lett. 112: 205-210.
Altschul et al. (1977) Nuc. Acids Res. 25:3389-3402.
Altschul et al. (1990) J. Mol. Biol. 215:403-410.
An et al. (1996) Plant J. 10, 107.
Aoyama and Chua (1997) Plant Journal 11:605-612
Ausubel et al. (1994) Current Protocols in Molecular Biology, Current Protocols, Vol. 1 and 2, USA.
Bennetzen & Hall (1982) J. Biol. Chem. 257, 3026-3031
Bendtsen et al. (2004) J. Mol. Biol., 340:783-795.
Bernhard, K. and Utz, R. (1993) "Production of *Bacillus thuringiensis* insecticides for experimental and commercial uses", In *Bacillus thuringiensis*, An Environmental Biopesticide: Theory and Practice, pp. 255-267, eds. Entwistle, P. F., Cory, J. S., Bailey, M. J. and Higgs, S., John Wiley and Sons, New York.
Beveridge et al. (1997) FEMS Microbiol Rev 20: 99-149
Bih et al. (1999), J. Biol. Chem. 274, 22884-22894.
Bravo et al. (1998) Appl. Environm. Microbiol. 64: 4965-4972
Brown (1998) *Molecular Biology LabFax*, Volumes I and II, Second Edition, Academic Press (UK)
Callis et. al. (1987) Genes Developm. 1:1183-1200
Cerón et al. (1994) Appl. Environ. Microbiol. 60: 353-356.
Cerón et al. (1995) Appl. Environ. Microbiol. 61: 3826-3831.
Christensen et al. (1992) Plant Mol. Biol. 18, 675-689.
Cordera et al. (1994) The Plant Journal 6, 141.
Cornejo et al. (1993) Plant Mol. Biol. 23, 567-581.
Cornelissen et al. (1986) EMBO J. 5, 37-40.
Crickmore et al. (1998). Microbiology and Molecular Biology Reviews 62: 807-813.
Crickmore et al. (2005). http://www.biols.susx.ac.uk/Home/Neil_Crickmore/Bt/index.html
Croy R. D. D. (1993) Plant Molecular Biology Labfax jointly published by BIOS Scientific Publications Ltd (UK) and Blackwell Scientific Publications, UK.
Datta et al. (1990) Bio/Technology 8, 736-740.
De Pater et al. (1992) Plant J. 2, 834-844.
Depicker et al. (1982) J. Molec. Appl. Genetics 1, 561-573.
Dieffenbach and Dveksler (1995) *PCR Primer: A Laboratory Manual*, Cold Spring Harbor Laboratory Press
Dulmage, H. T. (1981) "Production of Bacteria for Biological Control of Insects" in Biological Control in Crop Production, Ed. Paparizas, D.C., Osmun Publishers, Totowa, N.J., USA, pp. 129-141. struch et al. (1996) Proc Natl Acad Sci USA 93, 5389-94.
Estruch et al. (1996) PNAS USA 93(11), 5389-5394.
Franck et al. (1980) Cell 21, 285-294.
French et al. (1986) Anal. Biochem. 156, 417-423
Ffrench-Constant and Bowen (2000) Cell Mol Life Sci 57, 828-33.
Fromm et al. (1990) Bio/Technology 8, 833-839
Gardner et al. (1981) Nucleic Acids Research 9, 2871-2887
Gielen et al. (1984) EMBO J. 3, 835-845
Gordon-Kamm et al. (1990) The Plant Cell 2, 603-618
Gould et al. (1991) Plant Physiol. 95, 426-434
Güereca and Bravo. (1999) Biochim. Biophys. Acta. 1429: 342-350
Harlow and Lane (1988) Antibodies: A Manual Laboratory, Cold Spring Harbor Lab Press NY
Henikoff and Henikoff (1992) Proc. Natl. Academy Science 89 (10):915-919
Hesse et al. (1989), EMBO J. 8 2453-2461.
Hill (1983) *Epilachna* spp. In: Agricultural Insect pests of the tropics and their control. Cambridge University press. pp 438. ISBN 0 521 24638 5.
Ho et al. (1989). Gene 77, 51-59.
Höfte et al. (1988) Appl. and Environm. Microbiol. 54, 2010-2017
Hull and Howell (1987) Virology 86, 482-493
Ibarra et al. (2003) Appl. Environm Microbiol. 69:5269-5274
Itakura et al. (1977). Science 198, 1056-1063.
Keil et al. (1986), Nucl. Acids Res. 14, 5641-5650.
Klösgen et al. (1989), Mol. Gen. Genet. 217, 155-161.
Klösgen and Weil (1991), Mol. Gen. Genet. 225, 297-304.
Kota et al. (1999) Proc. Natl. Acad. Sci. USA 96, 1840-1845.
Kotiranta et al. (1998) Infect Immunol. 66: 4895-4902.
Last et al. (1990) Theor. Appl. Genet. 81, 581-588
Lereclus et al. (1989) FEMS Microbiol. Lett. 60: 211-218.
Lereclus et al. (1995) Bio/Technology 13, 67-71.
Luckevich and Beveridge (1989) J. Bacteriol. 171, 6656-6667.
Mahillon et al. (1989), FEMS Microbiol. Letters 60, 205-210.
Maxam and Gilbert (1980) Methods in Enzymol. 65, 499-560.
McBride et al. (1995) Bio/Technology 13, 362
McPherson et al. (2000) *PCR—Basics: From Background to Bench*, First Edition, Springer Verlag, Germany
Mesnage et al. (1998) J. Bacteriol. 180: 52-58
Mesnage, S. et al. (2001) Microbiology 147: 1343-1351
Mignot et al. (2002) Mol. Microbiol. 43: 1615-1627
Morris et al. (1999), Biochem. Biophys. Res. Commun. 255, 328-333.
Msadek et al. (1990) J. Bacterial. 172: 824-834
Murray et al. (1989) Nucleic Acids Research 17(2), 477-498.
Nakamura et al. (2000) Nucl. Acids Res. 28, 292.
Needleman and Wunsch algorithm (1970) J. Mol. Biol. 48: 443-453
Neuhaus & Rogers (1998) Plant Mol. Biol. 38, 127-144.
Odell et al. (1985) Nature 313, 810-812.
Oelmuller et al. (1993) Mol. Gen. Genet. 237, 261-272.
Park et al. (1997) J. Biol. Chem. 272, 6876-6881.
Pei and Blaser. (1990) J. Clin Invest. 85: 1036-1043
Sambrook et al. (1989) Molecular Cloning. A laboratory Manual. Second Edition, Cold Spring Harbor Laboratory Press.
Sambrook and Russell (2001) *Molecular Cloning: A Laboratory Manual*, Third Edition, Cold Spring Harbor Laboratory Press, NY
Sanger (1977)Proc. Natl. Acad. Sci. USA. 74(12), 5463-5467.
Sára and Sleytr (2000) J. Bacterial. 182: 859-868
Schnepf et al. (1998) Microbiol. Mol. Biol. Rev. 62: 775-806.
Shcherban et al. (1995), Proc. Natl. Acad. Sci. USA 92, 9245-9249.

Shimamoto et al (1989) Nature 338, 274-276
Sleytr and Beveridge (1999) Trends in Microbiology 7, 253-260.
Stanssens et al. (1989) Nucleic Acids Research 12, 4441-4454.
Sun et al. (2001) Acta Microbiol Sin. 41: 141-147.
Sutliff et al. (1991) Plant Molec. Biol. 16, 579-591.
Tavladoraki et al. (1998), FEBS Lett. 426, 62-66.
Terashima et al. (1999), Appl. Microbiol. Biotechnol. 52, 516-523.
Travers et al. (1987) Appl. Environ. Microbiol. 53: 1263-1266.
Vaeck et al. (1987) Nature 328, 33-37.
Van Den Broeck et al. (1985) Nature 313, 358.
Van Rie et al. (1990) Science 247, 72.
Velten et al. (1984) EMBO J. 3, 2723-2730
Velten and Schell (1985), Nucleic Acids Research 13, 6981-6998
Verdaguer et al. (1998), Plant Mol. Biol. 37, 1055-1067
Von Heijne, Gunnar (1986) Nucleic Acids Research. 14:11, 4683-4690
Wada et al. (1990). Nucl. Acids Res. 18, 2367-1411.
Waterfield et al. (2001) Trends Microbiol 9, 185-91.
White et al. (1989). Trends in Genet. 5, 185-189
Wong et al. (1992), Plant Molec. Biol. 20, 81-93.
Xu et al. (2004) Parasitology Research 92(1):53-7.
Zhang et al. (1991) The Plant Cell 3, 1155-1165.

The invention claimed is:

1. A method for identifying a protein toxic to an insect, said method comprising the steps of screening insecticidal bacilli cultures for S-layer protein genes by PCR with primers specific for S-layer homology regions in SEQ ID NO: 1,
wherein said S-layer homology regions encode regions in the amino acid sequence of SEQ ID NO: 2, wherein the regions are from amino acid position 34 to 76, from amino acid position 95 to 136, and from amino acid position 162 to amino acid position 198;

isolating the S-layer protein gene and transforming bacteria with said S-layer protein gene; and screening the bacteria for expression of the S-layer protein gene,
wherein the screening is accomplished by using the transformed bacteria or purified or semi-purified S-layer proteins, which are tested for toxicity to said insect.

2. The method of claim 1, wherein said bacilli are negative for Cry or VIP genes in PCR analysis.

* * * * *